US009744250B2

(12) United States Patent
Martens et al.

(10) Patent No.: US 9,744,250 B2
(45) Date of Patent: Aug. 29, 2017

(54) CHEMICAL MODEL OF A NEURODEGENERATIVE DISEASE, METHOD FOR PREPARATION AND USES OF SAME

(71) Applicants: CENTRE NATIONAL DE LA RECHERCHE SCIENTIFIQUE, Paris (FR); UNIVERSITE PARIS-EST CRETEIL VAL DE MARNE, Creteil (FR)

(72) Inventors: Thierry Martens, La Queue en Brie (FR); Michaël Rivard, Creteil (FR); Céline Laurencé, Villeneuve Saint Georges (FR); Christophe Morin, Saint Maur des Fosses (FR); Sonia Lehri-Boufala, Maisons-Alfort (FR); Narimane Zeghbib, Valenton (FR)

(73) Assignees: CENTRE NATIONAL DE LA RECHERCHE SCIENTIFIQUE, Paris (FR); UNIVERSITE PARIS-EST CRETEIL VAL DE MARNE, Creteil (FR)

( * ) Notice: Subject to any disclaimer, the term of this patent is extended or adjusted under 35 U.S.C. 154(b) by 0 days.

(21) Appl. No.: 14/443,499

(22) PCT Filed: Nov. 19, 2013

(86) PCT No.: PCT/FR2013/052784
§ 371 (c)(1),
(2) Date: May 18, 2015

(87) PCT Pub. No.: WO2014/076439
PCT Pub. Date: May 22, 2014

(65) Prior Publication Data
US 2015/0328338 A1    Nov. 19, 2015

(30) Foreign Application Priority Data

Nov. 19, 2012   (FR) .................................... 12 60979

(51) Int. Cl.
| | |
|---|---|
| *G01N 33/00* | (2006.01) |
| *A61K 49/00* | (2006.01) |
| *C07D 213/65* | (2006.01) |
| *C07D 213/20* | (2006.01) |
| *G01N 33/50* | (2006.01) |
| *G01N 33/68* | (2006.01) |

(52) U.S. Cl.
CPC ........ *A61K 49/0008* (2013.01); *C07D 213/20* (2013.01); *C07D 213/65* (2013.01); *G01N 33/5058* (2013.01); *G01N 33/6893* (2013.01); *G01N 2800/2835* (2013.01)

(58) Field of Classification Search
None
See application file for complete search history.

(56) References Cited

U.S. PATENT DOCUMENTS 7,833,514 B2 *  11/2010  Supuran ................. A61K 31/18
                                                         424/9.1

OTHER PUBLICATIONS

Zhang et al., Hypoxia Inducible Factor-1 as a Target for Neurodegenerative Diseases. Curr Med Chem. Oct. 2011 I; 18(28): 4335-4343.*
Berchner-Pfannschmidt et al., Chelation of Cellular Calcium Modulates Hypoxia-inducible Gene Expression through Activation of Hypoxia-inducible Factor-1a. The Journal of Biological Chemistry vol. 279, No. 43, Issue of Oct. 22, pp. 44976-44986, 2004.*
Youngster et al., Evaluation of the Biological Activity of Several Analogs of the Dopaminergic Neurotoxin 1-Methyl-4-Phenyl-1,2,3,6-Tetrahydropyridine. J. Neurochem. 48, 929-934 (1987).*
Banerjee et al., Mitochondrial dysfunction in the limelight of Parkinson's disease pathogenesis. Biochim Biophys Acta. Jul. 2009 ; 1792(7): 651-663.*
Betarbet, R., et al., "Animal models of Parkinson's disease," *BioEssays*, Jan. 1, 2002, vol. 24, No. 4, pp. 308-318.
Blandini, F., et al., "Animal models of Parkinson's disease," *FEBS Journal*, Apr. 2012, vol. 279, No. 7, pp. 1156-1166.
Blesa, J., et al., "Classic and New Animal Models of Parkinson's Disease," Journal of *Biomedicine and Biotechnology*, Jan. 1, 2012, vol. 2012, Article ID 845618, pp. 1-10.
Chen, L.J., et al., "Chemical and Enzymatic Oxidation of Furosemide: Formation of Pyridinium Salts," *Chemical Research in Toxicology*, Dec. 1, 2007, vol. 20, No. 12, pp. 1741-1744.
Duty, S., et al., "Animal models of Parkinson's disease: a source of novel treatments and clues to the cause of the disease," *British Journal of Pharmacology*, Oct. 1, 2011, vol. 164, No. 4, pp. 1357-1391.
Wojtas, L., et al., "Conformation and interactions of 4-(pyridinium-1-yl)-phenolate betaine-dye and its cation in the crystalline state," *Journal of Molecular Structure*, Mar. 6, 2006, vol. 785, No. 1-3, pp. 14-20.
Zhao, S., et al., "An efficient ultrasonic-assisted synthesis of imidazolium and pyridium salts based on the Zincke reaction," *Ultrasonics Sonochemistry*, Apr. 1, 2010, vol. 17, No. 4, pp. 685-689.
Written Opinion in International Application No. PCT/FR2013/052784, Feb. 21, 2014, pp. 1-6.

* cited by examiner

*Primary Examiner* — Kevin Hill
*Assistant Examiner* — Arthur S Leonard
(74) *Attorney, Agent, or Firm* — Saliwanchik, Lloyd & Eisenschenk

(57) ABSTRACT

The invention concerns the use of pyridinium furosemide or one of the derivatives, analogs, salts, metabolites, or prodrugs thereof in the preparation of a chemical model of a neurodegenerative disease, preferably Parkinson's disease. The invention also concerns the corresponding chemical model and the uses of same, in particular in screening tests for identifying drug candidates.

10 Claims, 8 Drawing Sheets

A. Route of synthesis by reductive amination and anodic oxidation

B. Route of synthesis by transamination

CHEMICAL MODEL OF A NEURODEGENERATIVE DISEASE, METHOD FOR PREPARATION AND USES OF SAME

CROSS-REFERENCE TO RELATED APPLICATION

This application is the U.S. national stage application of International Patent Application No. PCT/FR2013/052784, filed Nov. 19, 2013.

FIELD OF THE INVENTION

The invention relates to the development and use of chemical models for the study of a neurodegenerative disease, particularly Parkinson's disease.

BACKGROUND

Parkinson's disease is the second most common neurodegenerative disease after Alzheimer's disease. Its prevalence increases with age, and reaches 1% to 2% of subjects over the age of 50. It is characterized by disabling motor symptoms such as akinesia, muscle rigidity, and tremor at rest. These clinical signs can be accompanied by non-motor disorders such as digestive, urinary, or cognitive disorders.

Motor disorders associated with Parkinson's disease are directly related to the degeneration of dopaminergic neurons in the substantia nigra.

The molecular phenomena underlying this neuronal degeneration have not been fully explained but it is suggested that oxidative stress, mitochondrial dysfunction, and abnormal protein aggregation play a key role in the pathogenesis of the disease. Postmortem histological examination of specimens from patients with Parkinson's disease has nearly systematically revealed the accumulation and aggregation of the alpha-synuclein protein within filamentous eosinophil inclusions—the Lewy bodies (Spillantini et al., PNAS, 1998, 95, 669-6473). These inclusions have mainly been detected in the cytoplasm of dopaminergic neurons of the substantia nigra. Remarkably, the Lewy bodies are observable even in the absence of mutations in the alpha-synuclein gene and are thus considered a key marker of Parkinson's disease. Lewy bodies have also been detected in diseases involving loss of brain dopaminergic neurons, such as Lewy body dementia.

The exact causes of Parkinson's disease remain unknown. Environmental factors—such as exposure to pesticides or heavy metals—have been proposed. In parallel, studies of familial forms of Parkinson's disease have identified several genes that are involved in disease onset. However, Parkinson's disease is sporadic in the vast majority of cases, suggesting a multifactorial etiology involving genetic predisposition and exposure to environmental factors.

There is no treatment that cures Parkinson's disease or significantly slows its progression, especially the neuronal degeneration (Seidl, Front Neurol, 2011, 2, 68). The only treatments currently available are designed to reduce the symptoms associated with this disease, such as tremors.

In this context, the development of cell and animal models remains essential to uncovering the mechanisms involved in Parkinson's disease and to developing cures and/or preventive treatments for this disease. One can refer to Betarbet et al. (Bioassays, 2002, 24, 308-318), Blesa et al. (Journal of Biomedicine and Biotechnology, 2012, Article ID 845618), or Blandini et al. (FEBS Journal, 2012, 279, 1156-1166) for a summary concerning animal models of Parkinson's disease.

These publications show that the modeling of Parkinson's disease generally includes the induction of a dopaminergic lesion in the substantia nigra, either chemically or genetically.

The chemical approach involves inducing certain essential biological characteristics of Parkinson's disease by exposing the animal to a chemical agent. 6-hydroxydopamine (6-OHDA) was the first chemical agent used to mimic Parkinson's disease. This model has many disadvantages, however; in particular, 6-OHDA must be administered intracranially and has acute toxicity. Also, administration of 6-OHDA causes neither the appearance of lesions in all areas of the brain involved in Parkinson's disease nor the formation of Lewy bodies. The 6-OHDA model was supplanted by the MPTP (1-methyl-4-phenyl-1,2,3,6-tetrahydropyridine)/MPP+ model, which is presently the best-characterized and most-used model. After administration, MPTP crosses the blood-brain barrier and is metabolized by the monoamine oxidases of the astrocytes in MPP+ (1-methyl-4-phenyl-2,3-dihydropyridinum), an inhibitor of mitochondrial complex I. MPP+ specifically targets the nigrostriatal dopaminergic neurons. In many species, including humans, exposure to MPTP leads to degeneration of the dopaminergic neurons in the substantia nigra and induces some of the symptoms associated with Parkinson's disease. This model has many limitations, however. It is generally very difficult to keep animals that have bilateral lesions induced by MPTP alive without administration of L-dopa or dopamine agonists. Also, this model does not simultaneously reproduce all the motor disorders associated with Parkinson's disease. Although the presence of alpha-synuclein aggregates in the form of inclusions has been reported in some primate species, Lewy body formation has never been observed to date (Blesa et al., supra). Finally, the MPTP/MPP+ model is an "acute" model which does not reproduce the slow progression of Parkinson's disease; this makes it difficult to use it to discover new treatments or to define all the biological mechanisms involved in the onset of Parkinson's disease.

More recently, other chemical models based on an herbicide such as pyridinium, paraquat, or other inhibitors of mitochondrial complex I have been evaluated. These models have limitations similar to those of MPTP, particularly a lack of specificity towards the dopaminergic system.

Genetic models based on extinction, mutation, or overexpression of a gene of interest such as alpha-synuclein or LRRK2 (leucine-rich repeat kinase 2) have also been developed. Although these are interesting tools for analysis, they do not provide a completely accurate reproduction of the disease, especially the appearance of Lewy bodies (Dawson et al., Neuron, 2010, 66(5): 646-61). Furthermore, the presence of a genetic mutation in an animal from birth, and even in early embryogenesis, can involve many processes and induce compensation and adaptation phenomena which are not observable in the adult individual, which limits and complicates any transposition of the results to humans.

None of the chemical or genetic models developed so far are capable of reproducing all the symptoms and main markers of Parkinson's disease, especially its progressive development and the appearance of Lewy bodies.

Therefore, there is currently a need for animal and cell models of Parkinson's disease that provide alternatives to those described in the prior art.

SUMMARY OF THE INVENTION

The invention concerns the use of a compound of formula (I):

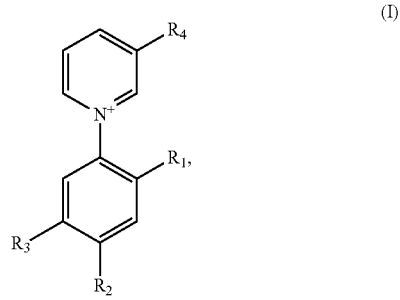

wherein:
- $R_1$ represents a hydrogen atom, a halogen atom, a $C_1$-$C_4$ alkyl, —OH, —CN, —C(=O)NH$_2$, —CF$_3$, —C(=O)O$^-$, or —C(=O)O—$R_5$ where $R_5$ represents H or a $C_1$-$C_4$ alkyl,
- $R_2$ is —SO$_2$NH$_2$, a hydrogen atom, a halogen atom, a $C_1$-$C_4$ alkyl, —OH, —CN, —C(=O)NH$_2$, —CF$_3$, or —C(=O)OR$_6$ where $R_6$ represents a $C_1$-$C_4$ alkyl or —H,
- $R_3$ is H, a halogen atom, a $C_1$-$C_4$ alkyl, —OH, —CN, —C(=O)NH$_2$, —CF$_3$, or —C(=O)OR$_7$ where $R_7$ represents —H or a $C_1$-$C_4$ alkyl and
- $R_4$ represents a hydrogen atom, —OH, or —OCH$_3$, or a pharmaceutically acceptable salt thereof, in the preparation of a chemical model of a synucleinopathy, preferably Parkinson's disease. The chemical model is obtained by placing a cell system in contact with said compound, said cell system being selected from among a cell, a cell culture, a tissue, and a non-human animal.

A further object of the invention is a method for preparing a chemical model of a synucleinopathy, preferably Parkinson's disease, comprising a step of placing a cell system, selected from among a cell, a cell culture, a tissue, and a non-human animal, in contact with a compound selected from among the compounds of formula (I) as defined above, pharmaceutically acceptable salts thereof, and combinations of these.

In certain embodiments, the chemical model is a cell model obtained from nervous tissue, preferably brain tissue, an organotypic culture obtained from brain tissue, a culture of nerve cells, for example neurons that are preferably dopaminergic and/or glial cells, or a cell line, preferably of neuronal origin. For example, the chemical model can be obtained from a cell line selected from the group consisting of cell lines SH-SY5Y, SK-N-MC, and PC12.

In other embodiments, the chemical model is a non-human animal, preferably selected from the group consisting of a mammal, an invertebrate such as C. elegans, and a fish such as the zebrafish.

The invention also relates to a chemical model of a synucleinopathy obtained by the method described above.

This chemical model can be used for implementing a screening test for compounds intended for the treatment or prevention of said synucleinopathy, preferably Parkinson's disease, or for evaluating the effectiveness of a drug substance in the treatment or prevention of said synucleinopathy, said model then preferably being a non-human mammal model.

A further object of the invention is a method for evaluating, screening, or selecting a compound for the treatment or prevention of a synucleinopathy, preferably Parkinson's disease, said method comprising:
a) placing a cell system in contact with a compound as described above, preferably furosemide pyridinium,
b) placing said cell system in contact with the compound to be tested, and
c) detecting or quantifying a marker characteristic of the synucleinopathy in order to determine the effectiveness of the test compound,
step b) possibly being implemented simultaneously with, before, or after step a), or overlapping step a).

Said cell system is selected from among a cell, a cell culture, a tissue, and a non-human animal, and step a) is implemented under conditions allowing the chemical model of the invention to be obtained in the absence of the test compound.

In some embodiments of the method, the cell system is selected from the group consisting of nervous tissue, preferably brain tissue, an organotypic culture obtained from brain tissue, a culture of nerve cells, for example, neurons, preferably dopaminergic and/or glial cells, and a cell line, preferably of neuronal origin such as the SH-SY5Y cell line, and the marker is selected from the group consisting of an intracellular accumulation of a synuclein, preferably α-synuclein, a marker of apoptotic cell death, preferably an increase of caspase activity, a decrease in cell survival rate, a decrease in activity of the mitochondrial respiratory chain, and combinations thereof.

In other embodiments of the method, the cell system is a non-human animal and the marker characteristic of the synucleinopathy is selected from the group consisting of a motor disorder, particularly a movement disorder or a decrease in rate of movement, a degeneration of dopaminergic neurons, the intracellular accumulation of alpha-synuclein in a dopaminergic neuron, a decrease in mitochondrial activity, particularly of complex I, and combinations thereof.

A further object of the invention is a kit for implementing a method for evaluating, screening, or selecting a compound intended for the treatment or prevention of a synucleinopathy, as described above, or for the preparation of a chemical model as described above, comprising:
- a compound as previously described, preferably furosemide pyridinium or one of its pharmaceutically acceptable salts, and
- a cell system selected from among a cell, a cell culture, a tissue, and a non-human animal, to be placed in contact with the compound in order to obtain said chemical model.

In the method or kit according to the invention, the cell system may be, for example, a nematode such as C. elegans or a zebrafish, including a larva thereof.

The invention also relates to the use of a compound as described above, preferably furosemide pyridinium or one of its pharmaceutically acceptable salts, to induce in a non-human mammal one or more symptoms associated with Parkinson's disease, preferably selected from the group consisting of muscle rigidity, tremor at rest, postural instability, akinesia, sleep or arousal disorder, intracellular accumulation of alpha synuclein, preferably in the form of Lewy bodies, and degeneration of dopaminergic neurons of the substantia nigra.

The invention relates to the use of a compound as described above, preferably furosemide pyridinium or one of its pharmaceutically acceptable salts, as a control compound or as a standard compound in a test for evaluating the toxicity, preferably neurotoxicity, of compounds, for example of environmental pollutants.

Lastly, the invention also concerns a compound of formula (I):

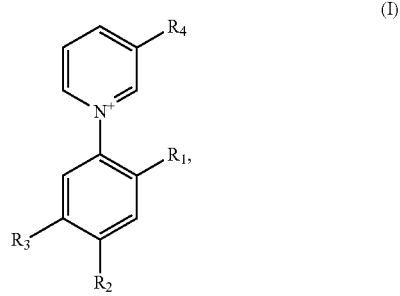

wherein:
R$_1$ represents a hydrogen atom, a halogen atom, a C$_1$-C$_4$ alkyl, —OH, —CN, —CF$_3$—C(=O)NH$_2$, —C(=O)O$^-$, or —C(=O)O—R$_5$ where R$_5$ represents H or a C$_1$-C$_4$ alkyl, R$_2$ is —SO$_2$NH$_2$, a hydrogen atom, a halogen atom, a C$_1$-C$_4$ alkyl, —OH, —CN, —C(=O)NH$_2$, —CF$_3$, or —C(=O)OR$_6$ where R$_6$ represents H or a C$_1$-C$_4$ alkyl, R$_3$ is H, a halogen atom, a C$_1$-C$_4$ alkyl, —OH, —CN, C(=O)NH$_2$, CF$_3$, or —C(=O)OR$_7$ where R$_7$ represents H or a C$_1$-C$_4$ alkyl, and R$_4$ represents a hydrogen atom, —OH, or —OCH$_3$, with the proviso that R$_2$ is not —SO$_2$NH$_2$ when R$_1$ represents —C(=O)O$^-$ or —(C=O)OH, R$_3$ is —Cl and R$_4$ is OH, or a pharmaceutically acceptable salt thereof.

BRIEF DESCRIPTION OF THE FIGURES

FIG. 1A shows the dose-response curves for:

the cell survival rate of the SH-SY5Y cell line after incubation for 24 h in the presence of furosemide pyridinium (black squares), and the cell survival rate of the SH-SY5Y cell line after incubation for 6 h in the presence of MPP+ plus 18 h with no MPP+ (white circles).

The cell survival rate was determined by the MTT viability assay as detailed in the examples. The results are normalized to the absorbance obtained for SH-SY5Y cells unexposed to furosemide pyridinium or MPP+.

Y-axis: % absorbance at 550 nm, X-axis: logarithm of the concentration of furosemide pyridinium or MPP+ expressed in μM.

Figure 1A:
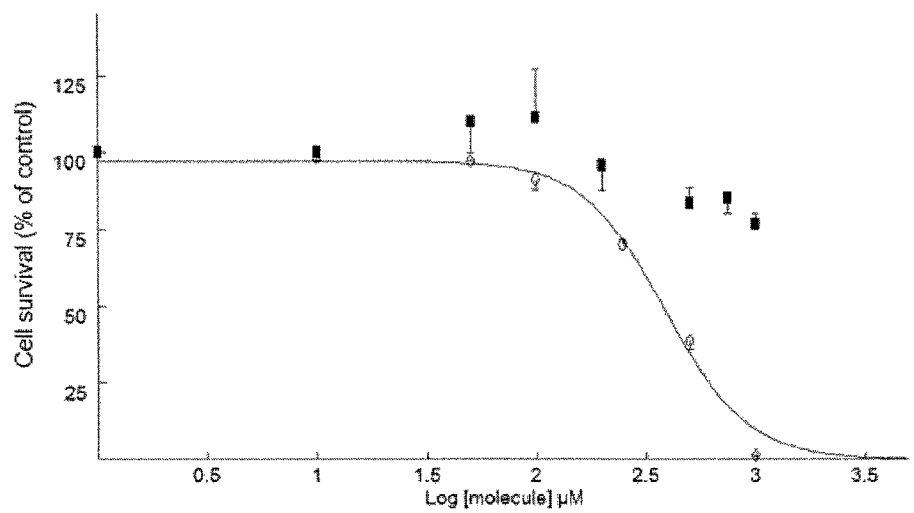
Figure 1B:
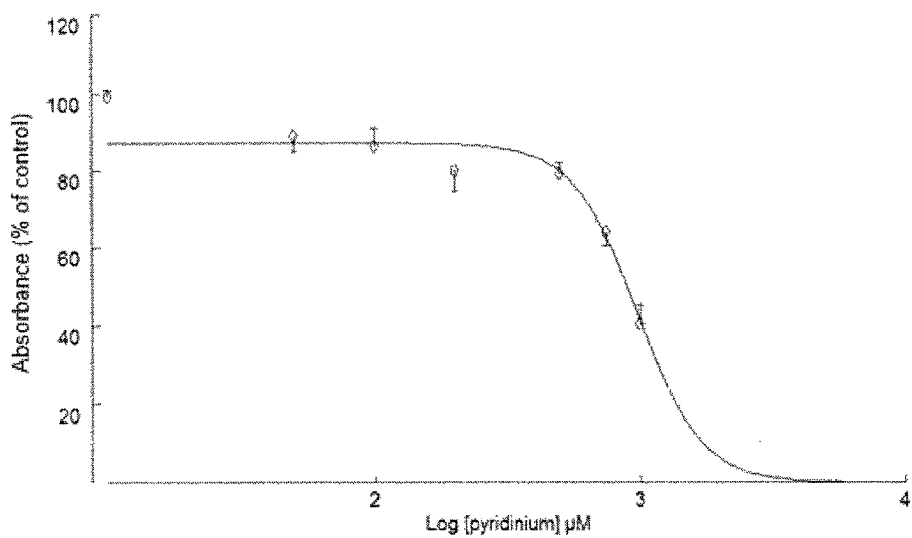

FIG. 1B shows the dose-response curve for the concentration of furosemide pyridinium versus the cell survival rate of the SH-SY5Y cell line after incubation for 96 h. The cell survival rate was determined by the MTT viability assay as detailed in the examples. The results are normalized to the absorbance obtained for SH-SY5Y cells unexposed to furosemide pyridinium.

Y-axis: % absorbance at 550 nm, X-axis: logarithm of the concentration of furosemide pyridinium expressed in μM.

Figure 1C:
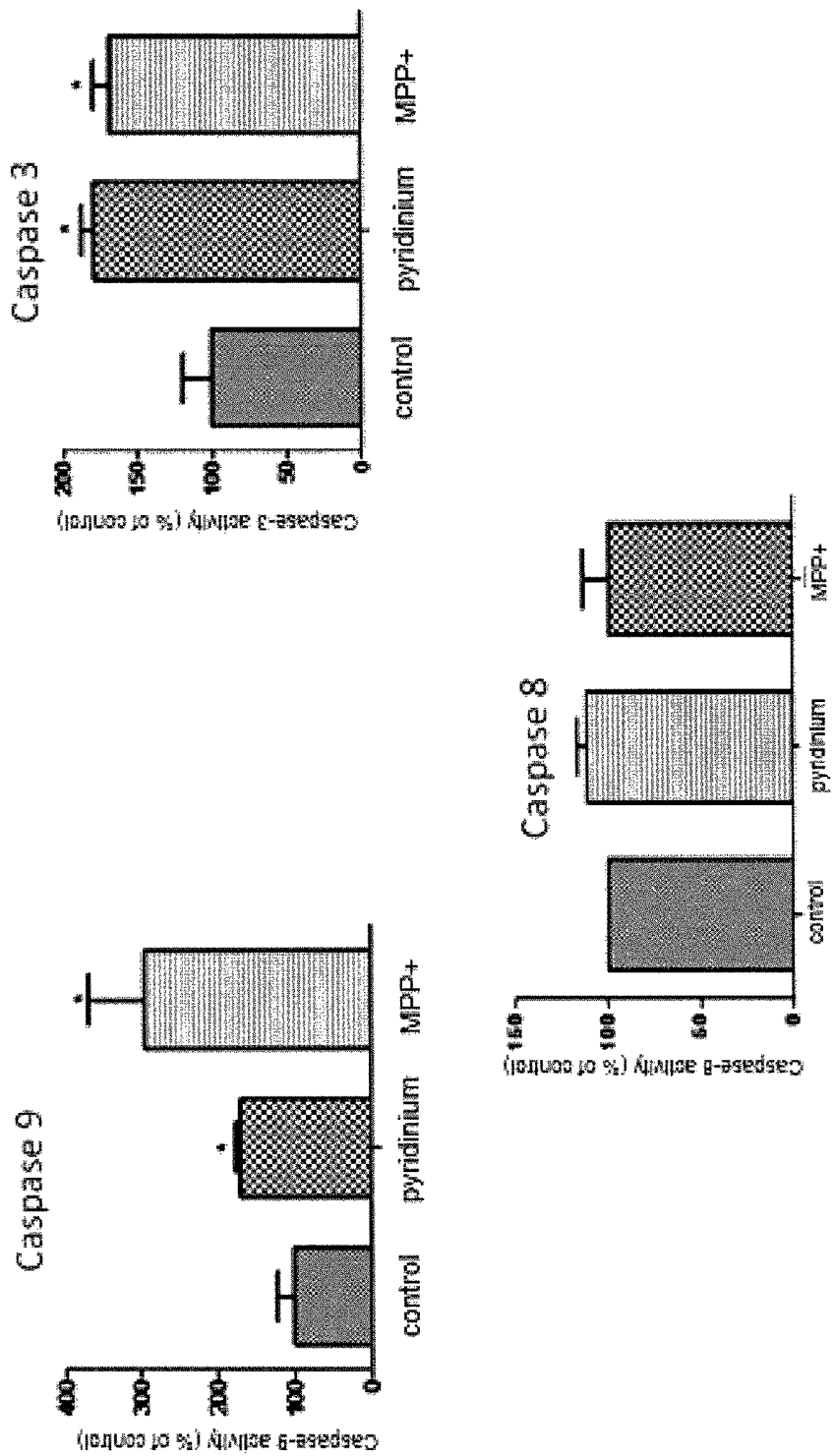

FIG. 1C shows 3 diagrams illustrating the caspase activity detected in the control experiment (control) after incubation with furosemide pyridinium (pyridinium) for 96 h or after incubation with MPP+ (MPP+) for 24 h. Y-axis: caspase activity as a percentage relative to the control experiment. Top left diagram: caspase 9. Top right diagram: caspase 3. Bottom diagram: caspase 8.

Figure 2A:
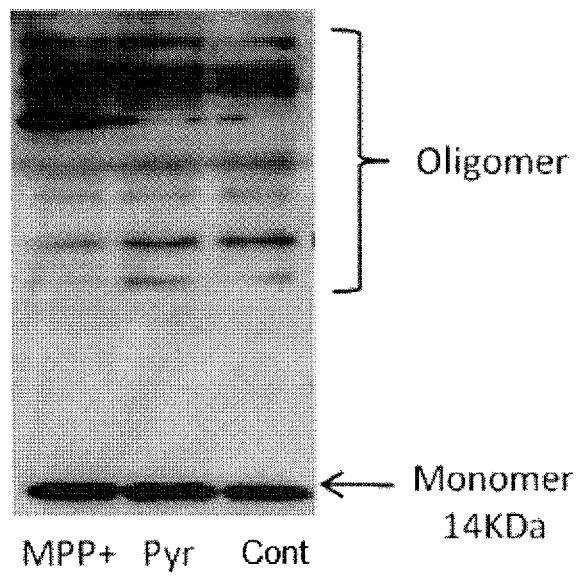

FIG. 2A shows the gel obtained by Western blot after visualization by an anti-synuclein primary antibody and a secondary antibody conjugated to HRP for SH-SY5Y cells incubated in the presence of MPP+ for 24 h, furosemide pyridinium for 96 h, or no compound. CONT: control, MPP+: MPP+, pyridinium: furosemide pyridinium, oligomer: oligomeric alpha-synuclein, monomer: monomeric alpha-synuclein.

Figure 2B:
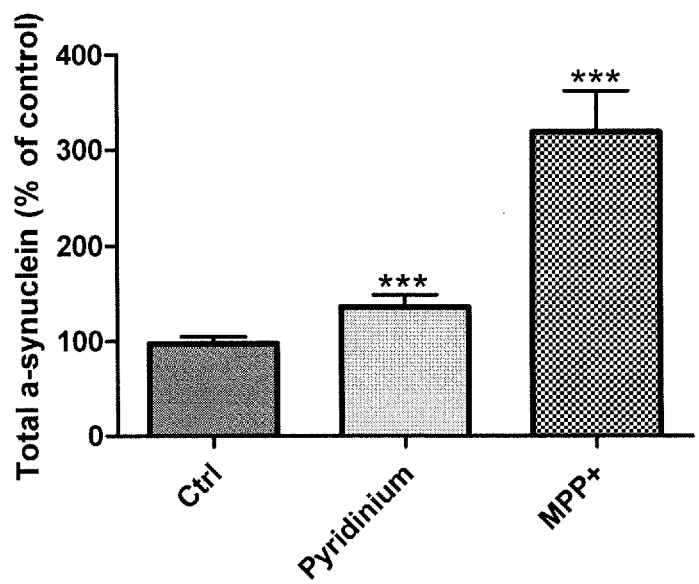

FIG. 2B is a diagram showing the relative amount of α-synuclein accumulated by the cells after incubation with furosemide pyridinium (pyridinium) for 96 h or after incubation in MPP+ for 24 h in comparison to the amount of α-synuclein present in the control cells (Ctrl). Y-axis: percentage of α-synuclein relative to the amount detected in the control cells—quantification of Western blot gels.

Figure 3A:
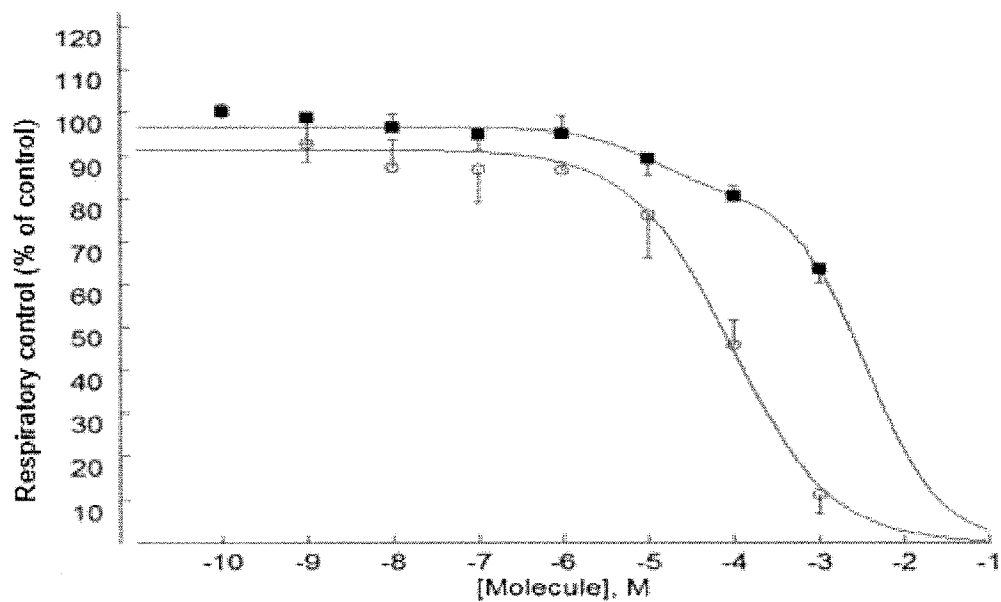

FIG. 3A shows the dose-response effect of MPP+ (white circles) or furosemide pyridinium (black squares) on the respiratory control of mitochondria isolated from rat cerebral cortex. Y-axis: respiratory control percentage (%), expressed relative to the control experiment (mitochondria not exposed to the compounds). X-axis: logarithm of the concentration in mol.

Figure 3B:
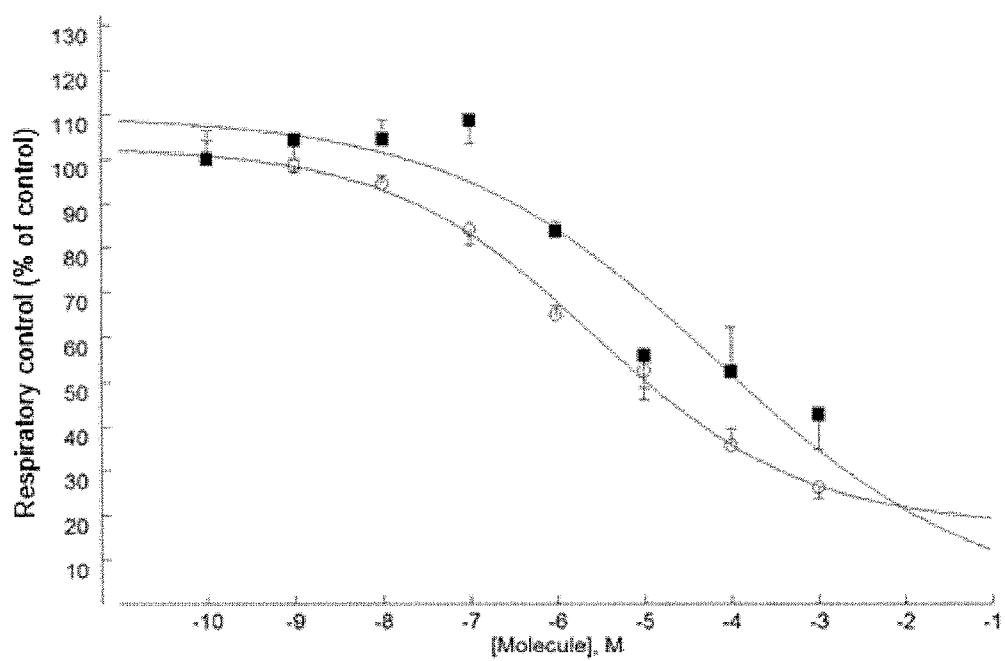

FIG. 3B shows the dose-response effect of MPP+ (white circles) or furosemide pyridinium (black squares) on the respiratory control of mitochondria isolated from rat striatum. Y-axis: respiratory control percentage (%), expressed relative to the control experiment (mitochondria not exposed to the compounds). X-axis: logarithm of the concentration in mol.

Figure 4A:
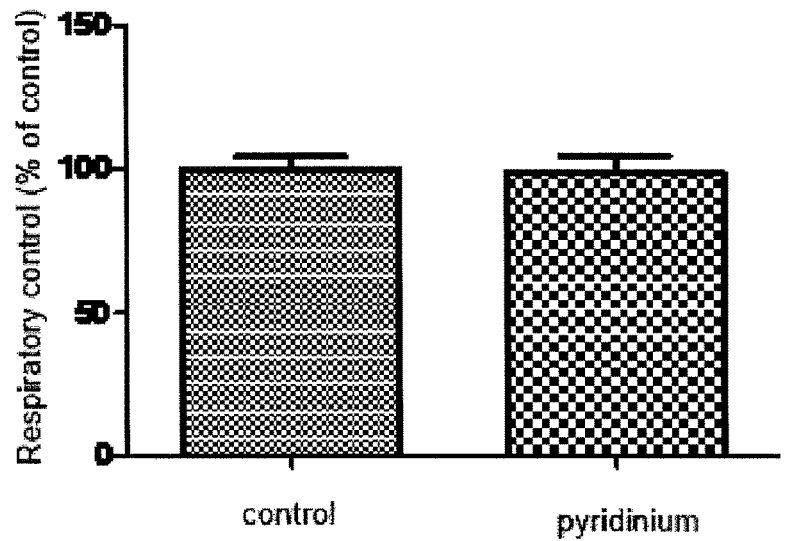

FIG. 4A is a diagram showing the respiratory control percentage of the control mitochondria and of those exposed to furosemide pyridinium after induction of complex II by succinate and inhibition of complex I by rotenone.

Figure 4B:
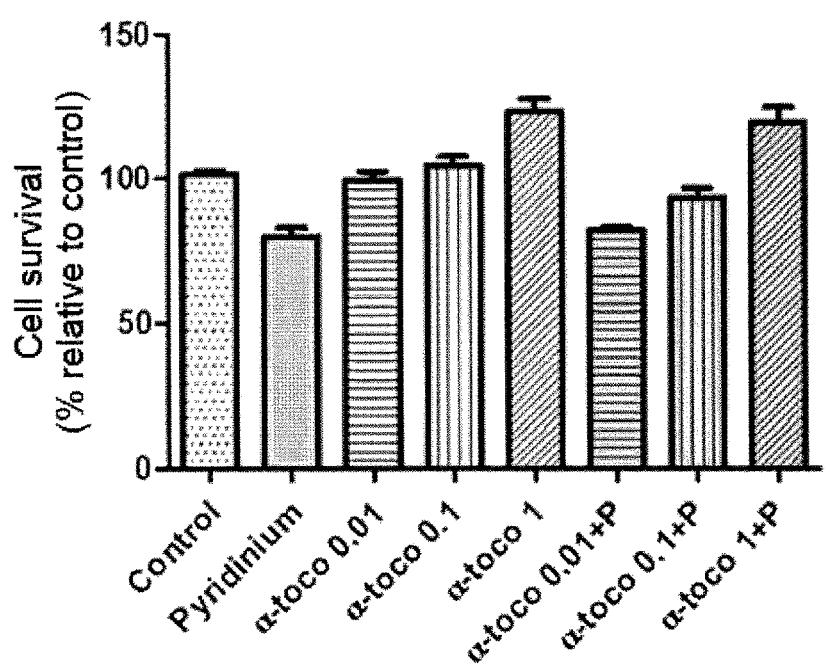

FIG. 4B is a diagram showing the percentage of cell survival, relative to control cells (control), of SH-SY5Y cells which have undergone different treatments. From left to right: control; incubation with 0.5 mM furosemide pyridinium (pyridinium); pre-incubation with 0.01 μg/ml α-tocopherol (α-toco); pre-incubation with 0.1 μg/ml α-tocopherol; pre-incubation with 1 μg/ml α-tocopherol; pre-incubation with 0.01 μg/ml α-tocopherol+incubation with 0.5 mM furosemide pyridinium; pre-incubation with 0.1 μg/ml α-tocopherol+incubation with 0.5 mM furosemide pyridinium; and pre-incubation with 1 μg/ml α-tocopherol+incubation with 0.5 mM furosemide pyridinium. (Pre-incubation period with α-tocopherol: 24 h, incubation period with furosemide pyridinium: 96 h).

Figure 5:
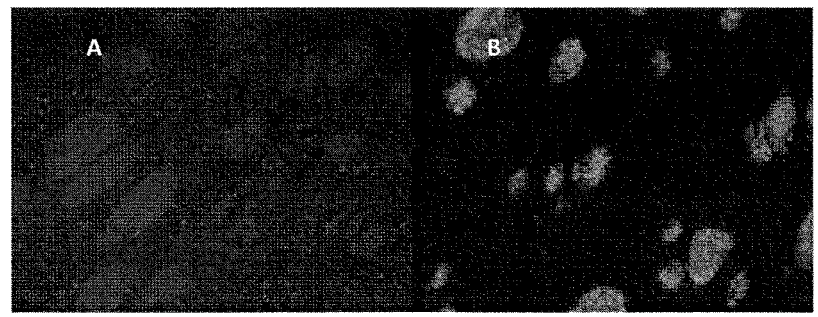
Figure 6:
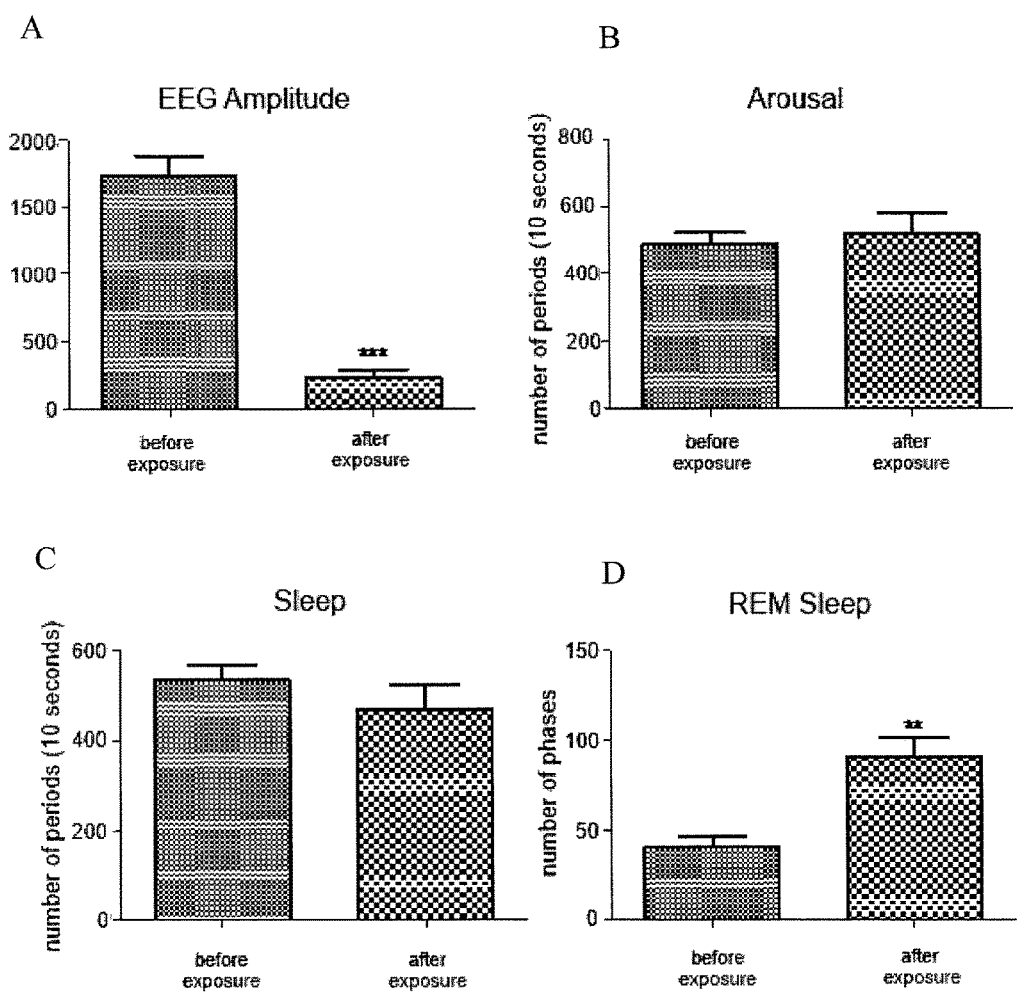

FIGS. 5 and 6 illustrate the effects of furosemide pyridinium administration in rats, for a daily oral dose of 20 mg/kg for 7 days. The rats were sacrificed 5 weeks after the last administration of furosemide pyridinium (see Examples, Part C, point 1).

FIG. 5 shows immunostaining of coronal sections of the striata of rats unexposed to furosemide pyridinium (FIG. 5A) and exposed to furosemide pyridinium (FIG. 5B) with an anti-alpha-synuclein antibody. The labeling of alpha-synuclein in sections from rats exposed to furosemide pyridinium (FIG. 5B) is significantly greater than what is observed for sections from non-treated rats and reveals the presence of vesicles. Exposure to furosemide pyridinium therefore induces an accumulation of alpha-synuclein in the form of vesicles in the cerebral striatum.

FIG. 6 shows the results from recording the electroencephalogram (EEG) of a rat before administration of furosemide pyridinium ("before exposure" histograms) and five weeks after the furosemide pyridinium treatment ended ("after exposure" histograms). FIG. 6A: amplitude of the EEG; FIG. 6B: number of arousal periods (greater than 10 s); FIG. 6C: number of sleep periods (greater than 10 s); and FIG. 6D: number of phases of REM sleep. After exposure to furosemide pyridinium, there is a clear decrease in the amplitude of the EEG and an increase in the number of REM sleep phases.

Figure 7:
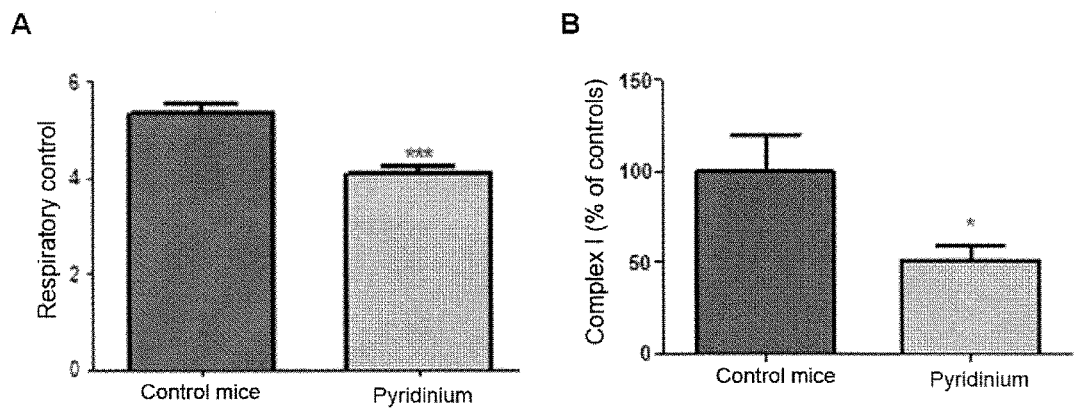
Figure 8:
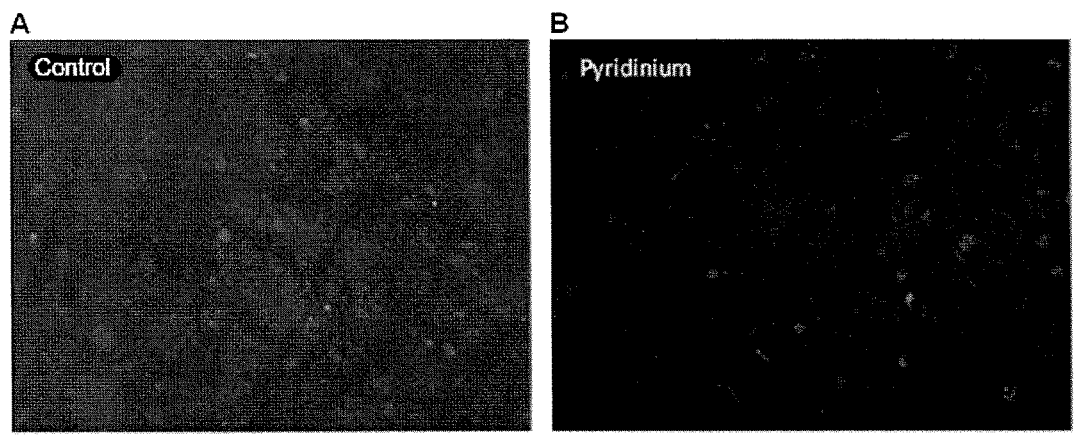
Figure 9:
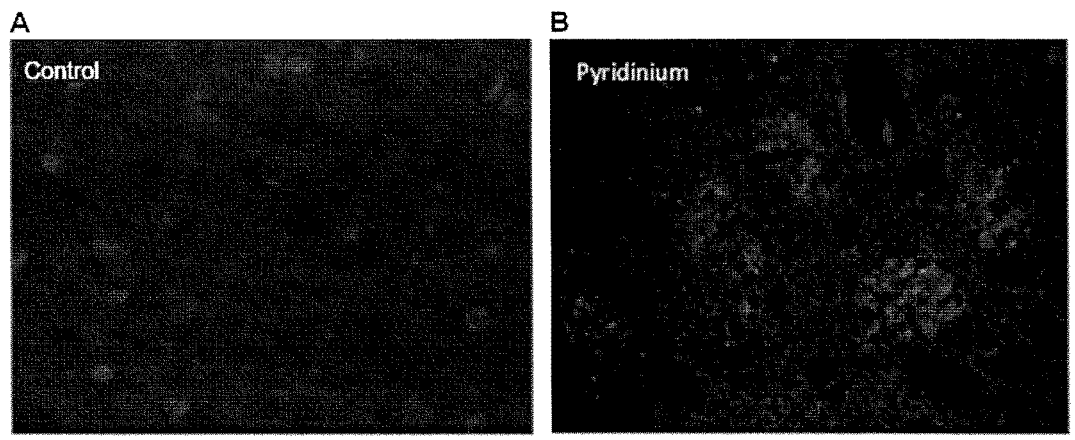

FIGS. 7 to 9 show the effects of administration of a daily dose of 20 mg/kg orally for 7 days in mice. The mice were sacrificed 30 days after the end of exposure to furosemide pyridinium (see Examples section, Part C, point 2).

FIG. 7 shows the level of activity of the respiratory chain (FIG. 7A) and of complex I (FIG. 7B) for mitochondria isolated from the striata of mice exposed to furosemide pyridinium compared to the activity levels measured for mitochondria from the striata of control mice. The mice that were exposed to furosemide pyridinium show a net decrease in respiratory control and in mitochondrial complex I. Exposure to furosemide pyridinium induces dysfunction of the mitochondrial respiratory chain in the striatum, which is still detectable 30 days after the end of exposure.

FIG. 8 shows the immunolabeling, by an anti-tyrosine hydroxylase antibody, of a coronal section from the striatum of a control mouse (FIG. 8A—control) and a coronal section from the striatum of a mouse exposed to furosemide pyridinium (FIG. 8B—pyridinium). The labeling of tyrosine hydroxylase for the coronal section of the mice exposed to furosemide pyridinium is much weaker than the labeling found for the coronal section of the control mouse.

FIG. 9 shows the immunolabeling, by an antibody against alpha-synuclein phosphorylated on Ser129, of a coronal section from the striatum of a control mouse (FIG. 9A—control) and of a coronal section from the striatum of a mouse exposed to furosemide pyridinium (FIG. 9B—pyridinium). The labeling of the phosphorylated alpha-synuclein is much greater for the coronal section of the mouse exposed to furosemide pyridinium than for the coronal section of the control mouse.

Figure 10:
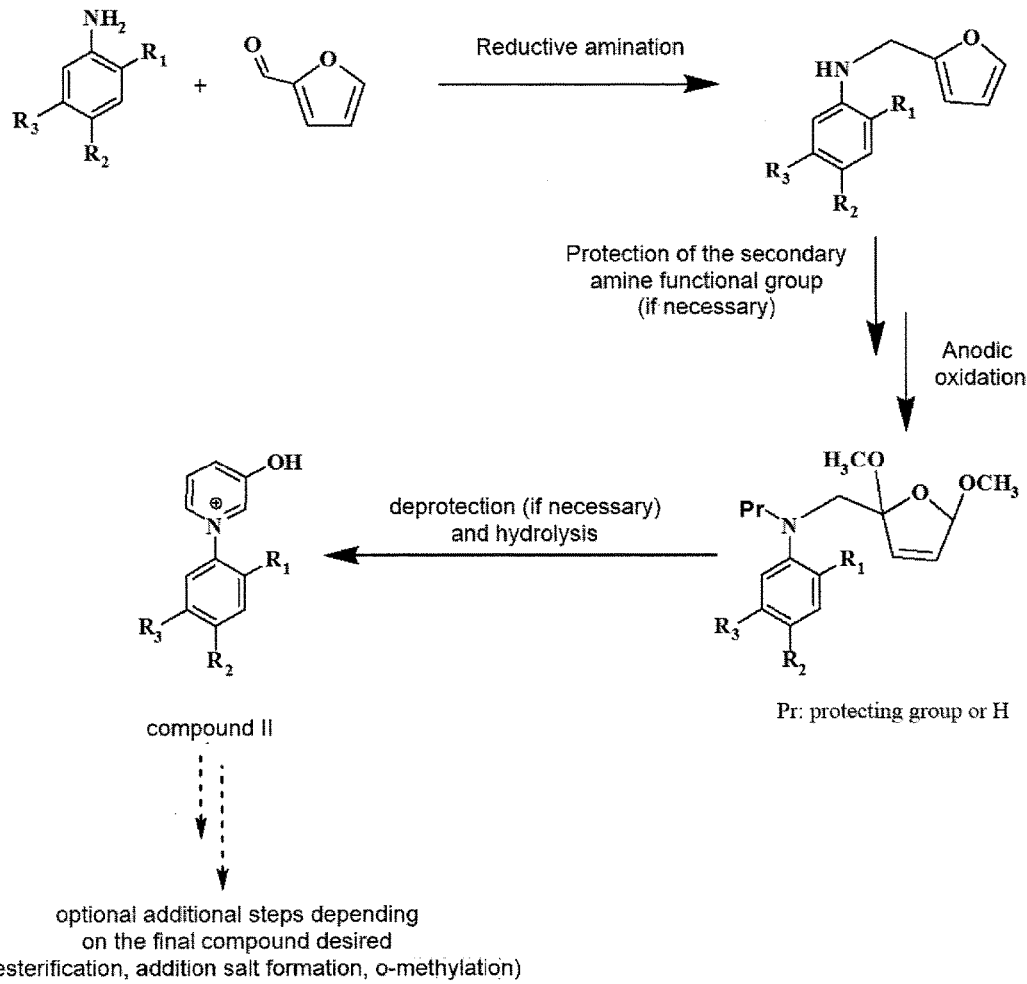
Figure 10:
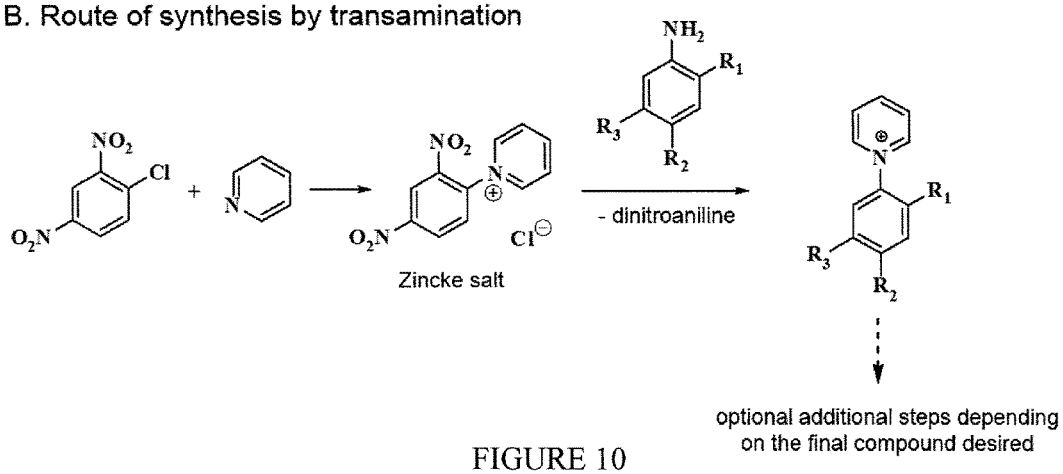

FIG. 10A shows a reaction diagram for the synthesis of compounds of formula (I) where $R_4$ is —OH or —OMe. After the reductive amination step, it is recommended that the secondary amine functional group be protected before starting the anodic oxidation step. Such a protection step is not necessary for the synthesis of furosemide pyridinium. Pr represents an amine protecting group or a hydrogen.

FIG. 10B shows a reaction diagram for the synthesis of compounds of formula (I) where $R_4$ is H.

The $R_1$, $R_2$, and $R_3$ groups are as defined in the description.

DETAILED DESCRIPTION OF THE INVENTION

Use of Furosemide Pyridinium, Method for Preparing a Chemical Model of a Neurodegenerative Disease, and Kit The present invention relates to a new chemical model of a neurodegenerative disease, preferably a synucleinopathy, based on the use of furosemide pyridinium, or one of its salts, prodrugs, metabolites, or derivatives, as a chemical agent.

Furosemide is a loop diuretic sold under the name of Lasix® for the treatment of hypertension and edema associated with congestive heart failure. It is excreted by the body primarily in unchanged form.

Its in vitro oxidation into a pyridinium derivative by liver microsomes was described by Chen et al. (Chem Res Toxicol, 2007, 20:1741-4). This pyridinium derivative (hereinafter referred to as furosemide pyridinium) is regarded as a potential metabolite of furosemide that can have diuretic activity. To the Applicant's knowledge, no other biological activity of furosemide pyridinium has been documented to date in the prior art.

Surprisingly, the Applicant showed that the pyridinium from furosemide displayed neurotoxicity in vitro, and more specifically that it reduced cell viability of the neuronal SH-SY5Y human cell line and did so in a dose-dependent manner. The Applicant clarifies that the SH-SY5Y line is a dopaminergic neuron cell model widely used and recognized by the scientific community.

The Applicant also showed that incubation of SH-SY5Y neuronal cells with furosemide pyridinium induced a clear increase in caspase-9 and caspase-3 activity, suggesting cell death involving the intrinsic mitochondrial pathway of apoptosis. Moreover, the Applicant observed that incubation with furosemide pyridinium induces in the cells an accumulation of α-synuclein with an appearance of oligomeric and dimeric entities. The Applicant also showed that pyridinium of furosemide affects the operation of the mitochondrial respiratory chain by selectively inhibiting complex I.

These results show that furosemide pyridinium is capable of inducing biological phenomena at the cellular level—inhibition of mitochondrial complex I, apoptotic cell death, and intracellular accumulation of α-synuclein—which are similar to those observed in the MPTP/MPP+ chemical model, which is the model of reference used for the study of Parkinson's disease. In other words, the pyridinium of furosemide induces phenomena at the cellular level that are analogous to those observed with MPP+.

However, furosemide pyridinium exhibits kinetics of toxicity significantly slower than MPP+ does. Indeed, incubation of SH-SY5Y cells for 96 h with furosemide pyridinium is necessary to obtain a rate of cell death similar to what is observed for an incubation of 6 h with MPP+. Such incubation with furosemide pyridinium induces a much smaller increase in intracellular levels of α-synuclein than what is observed in incubation with MPP+, but this rate is still significantly higher than that observed for the control experiment. In addition, furosemide pyridinium exhibits greater specificity for the mitochondrial complex I of the striatum than MPP+. These in vitro results were confirmed by in vivo studies conducted by the Applicant in rats and mice. Administration of a daily dose of 20 mg/kg furosemide pyridinium for seven days was not lethal, but led to dysfunction of the mitochondrial respiratory chain in the striatum and appearance of histological markers specific to Parkinson's disease, namely a specific intracellular accumulation of alpha-synuclein in the form of vesicles, in the striatum. In mice, the Applicant also demonstrated a pronounced increase in the expression of Ser129-phosphorylated alpha-synuclein which is the form primarily present in Lewy bodies in humans. To the Applicant's knowledge, such a result has not been observed to date for the other chemical models of Parkinson's disease.

The Applicant also observed the onset of sleep disorders in rats—namely an increase in the number of REM sleep phases—which can be observed in patients with a synucleinopathy.

Due to its lower toxicity and greater specificity for the striatum, the pyridinium of furosemide provides animal chemical models more accurately mimicking synucleinopathies, particularly with regards to progression, symptoms, and/or histological markers of these diseases. Furosemide pyridinium and its derivatives therefore have applications in the study of the progression—especially the early stages—of neurodegenerative diseases, particularly synucleinopathies, and in identifying new treatments to slow, stop, or even cure these diseases.

Thus, a first object of the present invention relates to the use of a chemical agent selected from the group consisting of furosemide pyridinium, a metabolite, a derivative, and a prodrug thereof, their salts, and combinations thereof in the preparation of a chemical model of a neurodegenerative disease.

"Furosemide pyridinium" is understood to mean the chemical compound having the following formula:

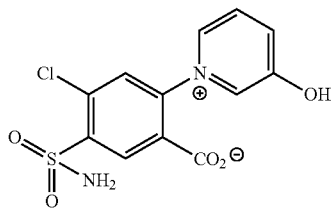

The chemical name of furosemide pyridinium is 4-chloro-2-(3-hydroxypyridinium-1-yl)-5-sulfamoylbenzoate. It should be noted that furosemide pyridinium is in the form of a zwitterion but may also be in the form of addition salts.

Furosemide pyridinium can be obtained from furosemide by anodic oxidation as described by the inventors in Laurence et al., Tetrahedron, 2011, 67, 9518-9521.

In the meaning of the invention, a "prodrug of furosemide pyridinium" refers to a compound of which the metabolism in vivo, or in vitro—meaning by a cell or cellular machinery—leads to the formation of furosemide pyridinium. "Cellular machinery" is understood to mean any protein, particularly any enzyme, organelle, or supramolecular complex (such as microsomes), obtained from a cell.

As an example, furosemide, which can be metabolized in vitro by liver microsomes, is a prodrug of pyridinium. Preferably, prodrugs of furosemide pyridinium are chosen from its esters.

The term "metabolite of furosemide pyridinium" is understood to mean any compound derived from metabolism in vitro or in vivo of furosemide pyridinium, said metabolite preferably presenting biological activities similar to those of furosemide pyridinium.

In the meaning of the invention, a "derivative of furosemide pyridinium" refers to a compound which structurally differs from furosemide pyridinium only in a minor structural modification. Preferably, said metabolite or derivative is capable, in vitro, of reducing the cell survival rate, increasing caspase activity, particularly caspase-3 and/or -9, inhibiting mitochondrial complex I, and/or inducing intracellular accumulation of alpha-synuclein in the SH-SY5Y cell line. The metabolite or derivative preferably has all four of these characteristics.

In certain embodiments of the invention, the chemical agent is a compound of formula wherein:
$R_1$ represents a hydrogen atom, a halogen atom, a $C_1$-$C_4$ alkyl, —OH, —CN, —C(=O)$NH_2$, —$CF_3$, —C(=O)$O^-$, or —C(=O)O—$R_5$ where $R_5$ represents —H or a $C_1$-$C_4$ alkyl,
$R_2$ is —$SO_2NH_2$, a hydrogen atom, a halogen atom, a $C_1$-$C_4$ alkyl, —OH, —CN, —C(=O)$NH_2$, —$CF_3$, or —C(=O)$OR_6$ where $R_6$ represents H or a $C_1$-$C_4$ alkyl,
$R_3$ is H, a halogen atom, a $C_1$-$C_4$ alkyl, —OH, —CN, —C(=O)$NH_2$, —$CF_3$, or —C(=O)$OR_7$ where $R_7$ represents H or a $C_1$-$C_4$ alkyl, and
$R_4$ represents a hydrogen atom, —OH, or —$OCH_3$,
or a pharmaceutically acceptable salt thereof.

In the meaning of the invention, a halogen atom encompasses Br, Cl, I, or F, preferably Br and Cl.

A $C_1$-$C_4$ alkyl group encompasses the methyl, ethyl, propyl, and butyl groups, preferably a methyl group.

It is understood that the chemical agent comprises the necessary counteranion(s) or countercation(s) depending on the ionization state of the groups $R_1$, $R_2$, $R_3$, and $R_4$.

In certain embodiments of the invention, the chemical agent is a compound of formula (I), wherein:
$R_1$ is —H, a halogen atom, —CN, —C(=O)$NH_2$, —$CF_3$, —C(=O)$O^-$, or —C(=O)$OR_5$ where $R_5$ represents —H or a $C_1$-$C_4$ alkyl,
$R_2$ is —C(=O)$NH_2$, —$SO_2NH_2$, a halogen atom, —H, —CN, or —$CF_3$,
$R_3$ is —H, a halogen atom, —CN, —$CONH_2$, —$CF_3$, —C(=O)$O^-$, or —C(=O)$OR_7$ where $R_7$ represents —H or a $C_1$-$C_4$ alkyl, and
$R_4$ is —OH, —OMe, or —H.

In other embodiments of the invention, the chemical agent is a compound of formula (I) wherein:
$R_1$ is —H, a halogen atom, —CN, —C(=O)$NH_2$, —$CF_3$, —C(=O)$O^-$, or —C(=O)$OR_5$ where $R_5$ represents —H or a $C_1$-$C_4$ alkyl,
$R_2$ is —C(=O)$NH_2$, —$SO_2NH_2$, a halogen atom, —H, —CN, or —$CF_3$,
$R_3$ is —H, a halogen atom, —CN, —$CONH_2$, —$CF_3$, and
$R_4$ is —OH, —OMe, or —H.

In another embodiment, the chemical agent is a compound of formula (I) wherein:
$R_1$ represents a hydrogen atom, —C(=O)$O^-$, or —C(=O)O—$R_5$ where $R_5$ is H or a $C_1$-$C_4$ alkyl group,
$R_2$ is —$SO_2NH_2$, —$CONH_2$, a hydrogen atom, or a halogen atom,
$R_3$ is —H or a halogen atom, and
$R_4$ is —OH, —OMe, or —H,
or a pharmaceutically acceptable salt thereof.

In certain embodiments, the chemical agent is a compound of formula (I) wherein $R_4$ is —OH. In particular, the chemical agent may be a compound of formula (Ia):

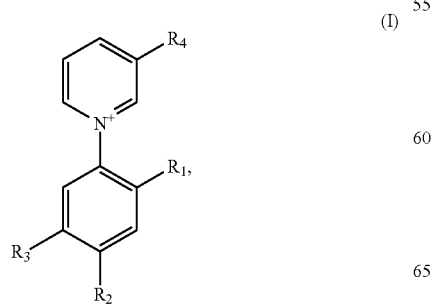

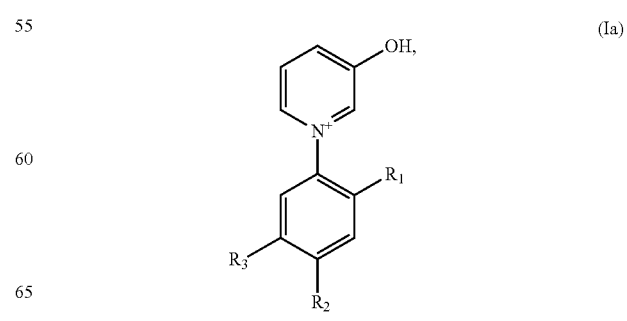

wherein:
R$_1$ represents a hydrogen atom, —C(=O)O$^-$, or —C(=O)O—R$_5$ where R$_5$ is H or a C$_{1-4}$ alkyl group,
R$_2$ is —SO$_2$NH$_2$, a hydrogen atom, or a halogen atom, and
R$_3$ is H or a halogen atom,
or a pharmaceutically acceptable salt thereof.

Of course, when R$_1$ is H or —C(=O)OR$_5$, the compound of formula (Ia) is associated with a pharmaceutically acceptable counteranion Q$^-$. As an example, Q$^-$ may be chosen from among Cl$^-$, Br$^-$, CH$_3$COO$^-$, or SO$_4^{2-}$.

When R$_1$ is COO$^-$, the compound is in zwitterion form and Q$^-$ is absent.

In one particular embodiment, the chemical agent is a compound of formula (Ia) wherein:
R$_1$ represents a hydrogen atom or —C(=O)O$^-$,
R$_2$ is —SO$_2$NH$_2$, a hydrogen atom, —Br, or —Cl, and
R$_3$ is H, —Br, or —Cl,
or a pharmaceutically acceptable salt thereof.

As an example, the chemical agent can be chosen from among the following compounds:

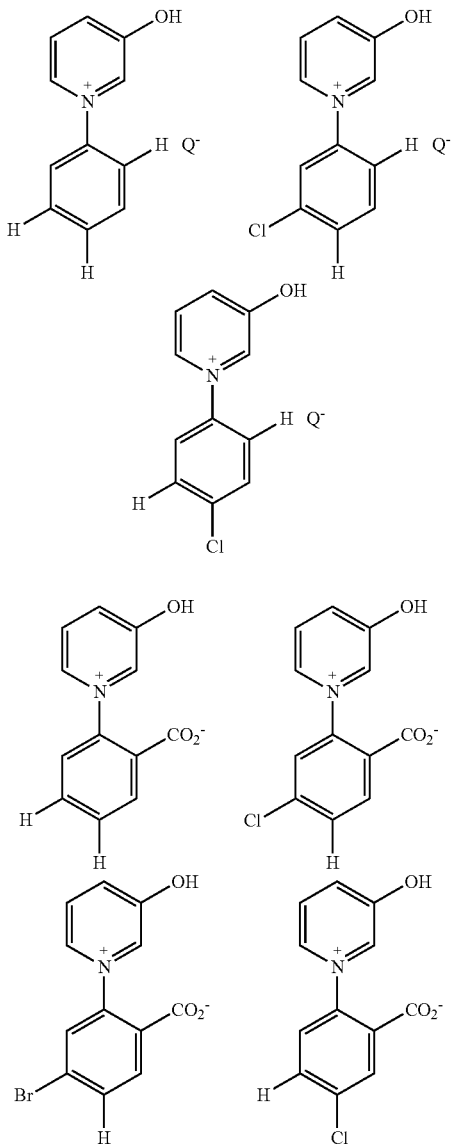

or the addition salts of the b) compounds.

The compounds of formula (I) where R$_4$ is —OH or —OMe can be obtained from derivatives of aniline or anthranilic acid which are commercially available or readily accessible by chemical synthesis. Typically, the aniline or anthranilic acid derivative undergoes a first step of reductive amination in the presence of furfural and then an electrochemical and/or chemical oxidation step resulting in a diacetal derivative. The diacetal derivative is converted into a pyridinium derivative (compound (II), FIG. 10) after intramolecular rearrangement by acid hydrolysis. Depending on the final compound desired, the pyridinium derivative may possibly undergo a step of esterification or methylation. After the reductive amination step, it is generally necessary to protect the secondary amine formed before carrying out the oxidation step. The protecting group is typically cleaved prior to the cyclization step. When the introduced protecting group is cleavable in acid medium, the deprotection and cyclization steps can be carried out simultaneously. A suitable protecting group for this is the BOC group (tert-butyloxycarbonyl). As illustrated in the Examples (see part A), it is not necessary to protect the secondary amine functional group for the synthesis of furosemide pyridinium.

The compounds of formula (I) where R$_4$ is —H can be obtained by transamination reaction. This synthetic route comprises preparing a Zincke salt by reaction of pyridine and 1-chloro-2,4-dinitrobenzene, and reacting said Zincke salt with an aniline derivative to obtain the desired pyridinium.

Preferably, furosemide pyridinium or one of its pharmaceutically acceptable salts is used for the implementation of the invention in its various aspects (see below).

In the following, the generic term "chemical agent" indicates a compound selected from the group consisting of furosemide pyridinium, a metabolite, a derivative, and a prodrug thereof, their salts, and combinations thereof, preferably a compound of formula (I) or (Ia) as described above, and even more preferably furosemide pyridinium or one of its pharmaceutically acceptable salts.

The term "neurodegenerative disease" is understood to mean any disease characterized by degeneration of one or more cell populations of the nervous system. In the context of the invention, the neurodegenerative disease is preferably characterized by a degeneration of a population of brain neurons. Examples of brain neurons of interest include the dopaminergic neurons of the substantia nigra or of the cerebral cortex. In a preferred embodiment of the invention, the neurodegenerative disease is a synucleinopathy.

For the purposes of the invention, the term "synucleinopathy" is understood to mean any neurodegenerative disease characterized by abnormal intracellular accumulation of synuclein. Preferably, the synuclein is alpha-synuclein, said alpha-synuclein accumulating as aggregates, for example, in the form of Lewy neurites and/or within cytoplasmic inclusions such as Lewy bodies. Synucleinopathies according to the invention include, but are not limited to, Parkinson's disease, multiple system atrophy, dementia with Lewy bodies, pantothenate kinase-associated neurodegeneration, Sanfilippo syndrome (Mucopolysaccharidosis type IIIA), or Niemann-Pick disease type C. In a preferred embodiment, the neurodegenerative disease is Parkinson's disease, in particular a sporadic form of Parkinson's disease.

The terms "chemical model of a disease" or "toxic model of disease" are understood to mean a cell system which, when placed in contact with a specific chemical agent, exhibits one or more biological mechanisms, one or more biomarkers, and/or one or more symptoms associated with said disease. "Placing in contact" or "exposure" indicate incubation of the cell system with the chemical agent, or administration of the chemical agent to the cell system.

In the specific context of the invention, the chemical agent capable of inducing the desired phenomena in the cell system is as described above, preferably a compound of formula (I).

In the meaning of the invention, a "cell system" refers to an entity selected from the group consisting of a cell, a cell culture, a tissue, or a non-human animal. For the purposes of the invention, a cell system and therefore a chemical model of the invention does not include humans, human embryos, or human embryonic stem cells.

In some embodiments, the chemical model of the invention may be a chemical cell model, in other words a eukaryotic cell, a cell culture, or a tissue. It is understood that the term "tissue" refers to a set of organized cells which has been isolated from a living being.

Preferably, the cellular chemical model is obtained from a cell culture, from a cell of neuronal origin, from a cell line preferably of neuronal origin, or from nervous tissue, preferably brain tissue.

In the meaning of the invention, a "cell culture" includes, without being limited thereto, a cell culture of a cell line, a primary culture, a mixed culture (or co-culture) comprising several cell types, and an organotypic culture.

The choice of cell culture or tissue will depend on the neurodegenerative disease, particularly the synucleinopathy being targeted.

To obtain a chemical cell model of Parkinson's disease, one may for example use a primary culture of dopaminergic neurons, an organotypic culture derived from brain tissue, a mixed culture comprising several cell types of neural origin, for example neurons and/or glial cells such as astrocytes and oligodendrocytes, or a cell line, preferably of neuronal origin, having one or more biochemical characteristics of dopaminergic neurons such as the expression of tyrosine hydroxylase, dopamine-beta-monooxygenase, and/or dopamine transporter. It may be a neuroblastoma cell line. Such cell lines include but are not limited to: human neuroblastoma cell line SH-SY5Y (ATCC number: CRL-2266), human neuroblastoma cell line SK-N-MC (ATCC number: HTB-10), or rat cell line PC12 (ATCC number: CRL-1721).

For an example usage of dopaminergic neurons in primary culture, one can refer to Schmidt, F., et al. (PLOS ONE, 2009, 4 (7): e6215).

In other embodiments, the chemical model of the invention is a chemical animal model obtained from a non-human animal. This may be an animal frequently used in pharmaceutical research or in pre-clinical trials. The animal may be a mammal, for example from the group consisting of a primate such as the baboon, macaque (for example rhesus macaque or crab-eating macaque), African green monkey, or chimpanzee, a rodent such as a mouse or rat, and a canid such as a dog.

Alternatively, the animal may be an invertebrate such as a *Drosophila* or a nematode, for example *Caenorhabditis elegans*, or a fish, such as the zebrafish (*Danio rerio*). Depending on the chemical model desired, a larva, juvenile, or an adult of these animals can be used.

The cell system may be a cell or a genetically modified organism. It may be a cell system into which a heterologous gene has been introduced to facilitate use of the final chemical model. For example, the cell system may be a zebrafish or *C. elegans* strain expressing a fluorescent marker such as GFP (Green Fluorescent Protein) at the dopaminergic neuron, controlled by a tissue-specific promoter. It may also be a transgenic strain having a genetic modification rendering it more sensitive to the chemical agent. For examples of transgenic animals suitable for the implementation of the invention, one can refer to Blandini et al. (supra), Chen et al. (Developmental Dynamics, 2009, 238, 746-754), or to Rubinstein (Expert Opinion Drug Metab, 2006, 2, 231-240).

In a second aspect, the present invention relates to a method for preparing a chemical model of a neurodegenerative disease, preferably a chemical model of a synucleinopathy, and more preferably a chemical model of Parkinson's disease.

The method for preparation according to the invention is characterized in that it comprises a step of placing a cell system as defined above in contact with the chemical agent, preferably selected from the group consisting of the compounds of formula (I), their salts, and combinations thereof.

In the context of the invention, "placing in contact" can refer to incubating the cell system with the chemical agent of interest, when said cell system is, for example, a cell, a cell culture, a tissue, or a small animal such as a nematode or zebrafish. In this embodiment, the cell system is placed in contact with a solution containing the chemical agent for a period ranging from a few minutes to several hours or even days. The incubation time may depend on the concentration of chemical agent in the solution. Typically, the incubation solution is a culture medium to which the chemical agent has been added at the desired concentration. The concentration of chemical agent is generally within a range of $1 \cdot 10^{-12}$ to $1$ mol·l$^{-1}$, preferably from $1 \cdot 10^{-10}$ to $1 \cdot 10^{-1}$ mol·l$^{-1}$. A range of $1 \cdot 10^{-10}$ to $1 \cdot 10^{-2}$ mol·l$^{-1}$ encompasses a range extending from $1 \cdot 10^{-10}$ to $1 \cdot 10^{-9}$, $1 \cdot 10^{-9}$ to $1 \cdot 10^{-8}$, $1 \cdot 10^{-8}$ to $1 \cdot 10^{-7}$, $1 \cdot 10^{-7}$ to $1 \cdot 10^{-6}$, $1 \cdot 10^{-6}$ to $1 \cdot 10^{-3}$, and $1 \cdot 10^{-3}$ to $1 \cdot 10^{-2}$ mol·l$^{-1}$.

Alternatively, when said cell system is a larger animal such as a rodent, primate, or canid, "placing in contact" corresponds to a step of administering the chemical agent to said cell system.

The chemical agent may be administered systemically or locally. Suitable routes of administration include, but are not limited to, oral, intravenous, intraarterial, intranasal, intradermal, subcutaneous, intramuscular, intraperitoneal, intracranial, and intraocular routes. The preferred routes of administration are oral, intravenous, subcutaneous, intraperitoneal, intranasal, and intracranial.

The dose and dosing regimen depend on the non-human animal used, particularly its weight, the chosen route of administration, and its sensitivity to the chemical agent and the desired effect. A person skilled in the art will know how to use routine tests, for example analysis of motor disorders developed by the animal or post-mortem histological studies, to determine the appropriate dose and dosing regimen. Typically, the daily dose to be administered can vary from 200 ng/kg to 100 mg/kg, preferably from 0.01 mg/kg to 30 mg/kg. The dosing regimen may comprise the administration of a single dose or of multiple doses over several hours or even days or weeks.

The chemical agent may be formulated with a pharmaceutically acceptable carrier—such as a saline or isotonic solution—or with one or more excipients such as a diluent, binder, stabilizer, emulsifier, adjuvant, etc. Alternatively, the chemical agent may be incorporated into the food or fluids provided to the animal.

According to a further aspect, the invention also relates to a kit for the preparation of a chemical model, said kit comprising:
  a chemical agent as described above, preferably selected from among the compounds of formula (I) or (Ia), their pharmaceutically acceptable salts, and combinations thereof, and a cell system to be placed in contact with the compound in order to obtain said chemical model.

The chemical agent may be furosemide pyridinium or one of its pharmaceutically acceptable salts. In some embodiments, the cell system is a primary neuronal culture, from a cell line preferably of neuronal origin, for example a neuroblastoma cell line, or nervous tissue, preferably brain tissue. Preferably, the cell system is a cell line with one or more biochemical characteristics of dopaminergic neurons. This may be one of the following cell lines: SH-SY5Y, SK-N-MC or PC12.

In other embodiments, the cell system is selected from among a nematode such as *C. elegans* or a fish, preferably a zebrafish, in the adult or larval state.

The kit may also include one or more consumables such as culture medium, buffer solution, a microplate, or an instruction booklet.

An additional object of the present invention is the use of the chemical agent as defined above to induce in a non-human mammal one or more disorders associated with Parkinson's disease. These symptoms are preferably selected from the group consisting of muscular rigidity, tremor at rest, postural instability, akinesia, intracellular accumulation of alpha-synuclein, preferably in the form of Lewy bodies in the cytoplasm of dopaminergic neurons of the striatum and/or in phosphorylated form, decrease in mitochondrial activity, particularly complex I, and degeneration of the dopaminergic neurons of the substantia nigra. These disorders are induced in animals in order to study the biological mechanisms involved in the development of Parkinson's disease or to evaluate the therapeutic efficacy of candidate drugs for the treatment or prevention of Parkinson's disease.

For the purposes of the invention, the term "treatment" means to slow or block the development of a disease or associated symptoms, or to cure the disease. Prevention of a disease means reducing the risk of the disease occurring within a given group of individuals.

Chemical Model of a Neurodegenerative Disease According to the Invention

A further object of the invention is the chemical model obtained by the method for preparation as described above. The chemical model of the invention differs from the cell system used to obtain it in that it has one or more characteristics that are not observed in said initial cell system.

When the chemical model is cellular, said chemical model is characterized in that it has one or more biochemical functions that are increased or decreased in comparison to the initial cell system. For example, the cellular chemical model of the invention can present an increase of caspase activity, particularly caspase-3 or -9, and/or a decrease of mitochondrial activity, particularly complex I, and/or an increase in the production and intracellular accumulation of alpha-synuclein in comparison to the initial cell system.

Preferably, the cellular chemical model of the invention has all three of these characteristics.

We will consider a biochemical function of the cellular chemical model to be distinct from that of the initial cell system if a quantitative variation of at least 10%, preferably at least 20%, or even at least 40%, is observed for this function. Quantification of biological functions in the chemical model and in the initial cell system can be achieved by any of the methods known to the skilled person. One can refer in particular to the examples in the present patent application.

When the chemical model is an animal model, said chemical model can be distinguished from the initial cell system by its having one or more anatomical or histological features and/or a behavioral phenotype that are distinct from those observed for the initial cell system. The animal chemical model according to the invention can thus have a degeneration of one or more neurons, preferably dopaminergic, and/or a cytoplasmic aggregation of alpha-synuclein. Additionally or alternatively, the animal model may have a separate behavioral phenotype, particularly a motor disorder such as decreased locomotor capabilities, meaning mobility, or a sleep or arousal disorder such as an increase in the number of REM sleep phases.

For example, it is expected that the chemical model obtained from *C. elegans* be characterized from a behavioral point of view by movement disorders, particularly slow and irregular movements accompanied by tremors, and from an anatomical point of view by a predominantly dopaminergic neuronal degeneration.

As a further example, it is expected that the chemical model obtained from larval zebrafish will present movement disorders, particularly a reduction in swimming speed, and dopaminergic neurodegeneration.

In the particular embodiment where the cell model is a mammal, said model may present a dopaminergic lesion of the substantia nigra and/or an intracellular accumulation of alpha-synuclein, possibly phosphorylated and/or in the form of Lewy bodies. It may also be characterized by one or more motor disorders selected from the group consisting of muscle rigidity, decreased mobility, particularly akinesia, postural instability, and tremor at rest. It may further present one or more non-motor symptoms such as sleep or olfaction disorders.

As another example, the chemical model obtained in the mouse presents, at post-mortem histological examination, a decreased expression of tyrosine hydoxylase and an accumulation of phosphorylated alpha-synuclein in the striatum. One will recall that to the Applicant's knowledge, no spontaneous case of Parkinson's disease has ever been reported for a non-human animal.

Usage of Chemical Models According to the Invention and Implementation Kits

Chemical models of the invention have numerous applications in basic research, particularly in studying the different stages of Parkinson's disease, especially the early stages. These chemical models also have applications in pharmaceutical research, particularly in identifying or evaluating new candidate drugs for the treatment or prevention of neurodegenerative diseases, particularly synucleinopathies, including Parkinson's disease.

The present invention therefore also relates to the use of a chemical model as described above in a screening test for compounds intended for the treatment or prevention of a neurodegenerative disease.

The invention also relates to the use of a chemical model as described above to evaluate the efficacy of a drug substance in the treatment or prevention of a neurodegenerative disease, the chemical model preferably being a non-human mammal.

In certain embodiments, the neurodegenerative disease is a synucleinopathy, preferably Parkinson's disease. It is understood that the chemical model used corresponds to the disease targeted by the screening test or candidate drug. For example, if searching for compounds for the treatment or prevention of Parkinson's disease, a chemical model corresponding to Parkinson's disease will be used.

In addition, the present invention relates to a method for evaluating, screening, or selecting a compound for the treatment or prevention of a synucleinopathy, preferably Parkinson's disease, said method comprising:
a) placing a cell system in contact with the chemical agent as described above,
b) placing said cell system in contact with the compound to be tested, and
c) detecting or quantifying a marker characteristic of the synucleinopathy,
where step b) may be implemented simultaneously, before, or after step a), or may overlap step a).

Step a) is carried out under conditions that allow the chemical model of the invention to be obtained if the test compound is not added (meaning there is no prior or simultaneous contact with the test compound).

Step c) is carried out to determine the potential efficacy of the compound. The term "efficacy" is understood to mean the ability of the compound to modulate the marker characteristic of the synucleinopathy in comparison to a control experiment or to previously obtained reference values.

The method according to the invention may thus comprise the steps of:
a) placing a cell system in contact with the chemical agent as described above in order to obtain a chemical model as defined above,
b) placing said cell system in contact with the test compound, and
c) detecting or quantifying a marker characteristic of the synucleinopathy, which allows the efficacy of the test compound to be determined,
where step b) may be implemented simultaneously, before, or after step a), or may overlap step a).

The cell system may be selected from the group consisting of a cell, a cell culture, a tissue, or a non-human animal, as described above.

The "placing in contact" steps of a) and b) can be achieved by incubation or by administration, depending on the cell system chosen.

Preferably, the chemical agent is selected from among the compounds of formula (I), their pharmaceutically acceptable salts, and combinations thereof. Even more preferably, the chemical agent is furosemide pyridinium or one of its pharmaceutically acceptable salts.

The method according to the invention may comprise one or more additional steps, in particular steps of washing or steps of treating the cell system.

In some embodiments, a control group is used, meaning a cell system that is subjected to all the steps described above but which is not placed in contact with the test compound.

Thus, in some embodiments, the method according to the invention comprises:
a) placing the cell system in contact with the chemical agent as described above,
b) placing said cell system in contact with the test compound, this contact being simultaneous with, preceding, following, or overlapping step a),
c) detecting or quantifying a marker characteristic of the synucleinopathy in said cell system, and
d) comparing the result obtained in step c) with the detection or quantification of said marker in a control cell system obtained by contact with the chemical agent in the absence of the test compound.

The comparison in step d) allows the test compound to be selected or rejected as a drug candidate. Examples are provided further below in the description.

Preferably, the chemical agent is furosemide pyridinium.

The term "marker characteristic of a disease" is understood to mean a biochemical, histological, anatomical, or behavioral modification associated with the disease, which is observed in an individual suffering from the disease or in a chemical or genetic model of this disease, in comparison to a healthy individual or an initially healthy cell system.

In some embodiments of the method of the invention, the cell system is a cell, a cell culture, or a nervous tissue, preferably a brain tissue. Preferably, the cell system is a cell line having one or more biochemical characteristics of dopaminergic neurons. For example, the cell line is selected from among the lines SH-SY5Y, SK-N-MC, and PC12.

In this embodiment, the marker characteristic of the synucleinopathy is preferably selected from the group consisting of the intracellular accumulation of a synuclein, preferably α-synuclein, a marker of apoptotic cell death, preferably an increase in caspase activity such as caspase-3 and/or -9 activity, a decrease in the cell survival rate, a decrease in the activity of the mitochondrial respiratory chain, particularly a decrease in the activity of mitochondrial complex I, and combinations thereof.

Quantification of these markers may be carried out according to techniques well-known to those skilled in the art. There is considered to be an increase or decrease in a marker when a variation is observed of at least ±10%, preferably at least ±20%, compared to the value of the marker quantified in the initial cell system (not exposed to the chemical agent).

For example, cell survival rates can be quantified by the MTT viability test. Caspase activity can be measured using a test based on the capacity of each caspase for specifically cleaving a fluorescent substrate (Yue et al., Cell Death Differ, 2009, 16(5):770-81). Quantitation of intracellular accumulation of alpha-synuclein can be carried out using anti-synuclein antibodies labeled or conjugated with an enzyme such as horseradish peroxidase, for example by Western blot as described in the examples or by an ELISA assay.

Decreased activity of the mitochondrial respiratory chain can be quantified by measuring the oxygen consumption of mitochondria using polarography and evaluating the coupling of oxidative phosphorylation in the presence of substrates of complex I or II, or by measuring the activity of complex I by spectrophotometry or the production of reactive oxygen species. Methods for measuring the decrease in mitochondrial activity are provided, for example, in Morin et al. (Neuroscience, 2002, 115(2):415-24) and Cormier et al. (Brain Res, May 4, 2001, 900(1):72-9).

In other embodiments, the cell system is a non-human animal. The marker characteristic of the synucleinopathy is selected from the group consisting of a motor disorder, especially a movement disorder, a sleep or arousal disorder, degeneration of dopaminergic neurons, intracellular accumulation of alpha-synuclein at a dopaminergic neuron, and combinations thereof.

If it is desired to evaluate a large number of compounds, for example as part of a high-throughput screening assay, preferably a cell system is used from the group consisting of a cell, a cell culture, a tissue, or a small animal such as a zebrafish or *C. elegans*.

The order of the contact steps a) and b) will depend on the type of compound that is to be identified.

If looking for a compound with protective activity or capable of slowing the progression of the disease, in a first step the test compound can be incubated with the cell system for one or several minutes or several hours, and then the chemical agent (for example furosemide pyridinium) is added to the medium. As an alternative, steps a) and b) can be simultaneous.

If looking for a compound with curative activity, the cell system can be placed in contact with the chemical agent (for example furosemide pyridinium), for example for a period of 24 h to 48 h, and then in a second step the test compound is added to the medium. The cell system may be washed before introduction of the test compound; in such case steps a) and b) are therefore successive.

When implementing steps a) and b) by incubation, the concentration of the chemical agent (for example furosemide pyridinium) and of the test compound are generally chosen within a range of $1 \cdot 10^{-10}$ to $1$ mol·L$^{-1}$, preferably $1 \cdot 10^{-8}$ to $1 \cdot 10^{-2}$ mol·L$^{-1}$.

In one particular embodiment, the cell system is a nematode, in particular *C. elegans*. In this case, those skilled in the art can refer to Braungart et al. (Neurodegenerative Disease, 2004, 1: 175-183) for the implementation of the method according to the invention.

In this embodiment, the marker characteristic of the synucleinopathy can be selected from a decrease in mobility or the degeneration of dopaminergic neurons. Methods for quantifying these two markers are described in Braungart et al. (see supra) which is incorporated herein by reference.

Quantification of the degeneration of dopaminergic neurons can be performed by using a strain of *C. elegans* specifically expressing GFP protein at the dopaminergic neurons, for example the strain cat-2::GFP. Quantification of dopaminergic degeneration is then achieved by measuring the fluorescence at an appropriate excitation wavelength.

For example, the method of the invention may be carried out on a microplate using the cat-2::GFP strain of *C. elegans* described by Lints et al. (Development, 1999, 126:5819-5831). A given number of nematodes suspended in an appropriate culture medium are distributed into each well of the microplate. The wells of the microplate are divided into four groups. In group 1, the nematodes are simultaneously incubated with furosemide pyridinium and the test compound. In group 2, the nematodes are incubated with furosemide pyridinium only. In group 3, the nematodes are not placed in contact with either pyridinium or with the test compound. Lastly, in group 4, the nematodes are incubated with the test compound only. The four groups are incubated for a sufficiently long period, typically for several hours or even days. After incubation, the mobility and/or the extent of neuronal degeneration are quantified. The values obtained for group 3 are used to normalize the results for groups 1 and 2 in the same microplate. The efficacy of the test compound is determined by comparing the results of group 2 with those obtained for group 1. The safety of the test compound can be verified by comparing the results obtained for group 4 with those obtained for group 3.

The test compound can be considered to be effective, and therefore selected, if it induces an increase of at least 10% in the average mobility and/or an increase of at least 10% in the fluorescence in the individuals in group 1 compared to the individuals in group 2.

In other embodiments, the cell system is a zebrafish, either in the adult or larval stage. The use of zebrafish in screening tests is well-known in the art and is described for example in the review article by Rubinstein (Expert Opin Drug Metab Toxicol, 2006, 231-240). One can, for example, use a zebrafish line expressing alpha-synuclein coupled to a GFP probe or a line having mutations in genes commonly involved in Parkinson's disease (PARKIN, LRRK2, DJ-1, etc.).

In an additional embodiment, the cell system is a non-human mammal as described above. Preferably, it is a primate or a rodent.

As is the case in smaller cell systems, the order of steps a) and b) of the method according to the invention depends on the type of compounds one wants to identify. Also, depending on the chosen dosing regimen, steps a) and b) may be repeated multiple times.

If looking for a compound with preventive activity or one that slows the development of the disease, the test compound may be administered to the animal before (typically a few hours before) the chemical agent (for example furosemide pyridinium). If looking for a compound with curative activity, the test compound can be administered to the animal after the chemical agent or simultaneously with it.

The test compound and the chemical agent may be administered by any route, preferably oral, intraperitoneal, intranasal, intravenous, subcutaneous, intramuscular, or intracranial. Routes of administration of the chemical agent and the test compound may be the same or different.

The doses to be administered depend on the animal used, particularly its weight, the chosen route of administration, and its sensitivity to the furosemide pyridinium and to the test compound. The skilled person will know how to determine the proper dosage and dosing regimen by using routine tests. Typically, the dose to be administered can vary from 200 ng/kg to 100 mg/kg. The dosing regimen may include the administration of a single dose of each compound or multiple doses over several hours, days, or weeks.

In this embodiment, the marker quantified or detected in the method of the invention may be an anatomical lesion, such as degeneration of the dopaminergic neurons of the substantia nigra, and the appearance of alpha-synuclein aggregation, for example in the form of Lewy neurites and/or Lewy bodies. The anatomical lesion may be detected by in vivo imaging, for example as described in PCT application WO2012/065045, or by postmortem histological analysis.

The marker of the synucleinopathy may also be a motor disorder such as muscle rigidity, decreased mobility, particularly akinesia, postural instability, or tremor. It should be noted that the motor disorder induced in the chemical model may depend on the animal used. The skilled person can refer to the work described in the prior art for determining the motor disorders to study in the animal chosen and how to quantify them.

A compound is considered active if it improves or prevents the onset of a motor disorder induced by furosemide pyridinium and/or if it prevents neurological lesion.

According to a further aspect, the present invention relates to a kit for implementing a screening method as described above, said kit comprising:

a chemical agent, preferably selected from the group of compounds of formula (I), their pharmaceutically acceptable salts, and combinations thereof, and a cell system as described above.

In certain embodiments, the cell system is a neuronal cell culture, a cell line, preferably of neuronal origin, or nervous tissue, preferably brain tissue.

The cell system may be, for example, a cell line with one or more biochemical characteristics of dopaminergic neurons. For example, the cell line may be selected from the cell lines SH-SY5Y, SK-N-MC, and PC12.

In other embodiments, the cell system is a non-human animal, preferably a nematode such as *C. elegans* or a fish such as the zebrafish, in the adult or larval state.

Advantageously, the cell system is selected from the group consisting of a cell line, a nematode such as *C. elegans*, and a fish such as the zebrafish, the fish and nematode being in the larval or adult state.

The kit of the invention may optionally comprise a means for the detection or quantification of a marker characteristic of the synucleinopathy, for example an anti-synuclein antibody.

The kit may also comprise one or more consumables, such as culture medium, buffer solution, a microplate, or reference or standard compounds, for use in carrying out the screening method. Finally, the kit may include an instruction booklet for performing the screening test.

For example, the kit may comprise, as a reference compound, an antioxidant such as alpha-tocopherol that can prevent the effect of the chemical agent.

Test for Evaluating Compound Neurotoxicity

Surprisingly, the Applicant has shown that furosemide pyridinium has cellular neurotoxicity that is detectable after a long incubation period of about 96 h. Such a result is particularly surprising in view of the toxicity tests currently used. To the knowledge of the Applicant, these tests specify periods of incubating the test compound with the reference cell model of at most 48 h. Furosemide pyridinium would therefore not have been identified as neurotoxic in these tests.

Furosemide pyridinium and its derivatives, metabolites, and prodrugs as described above, particularly the compounds of formula (I) or (Ia), may therefore be useful as a control compound, or as a standard compound, for use in a test for evaluating the toxicity of compounds, for example environmental pollutants.

The invention therefore also relates to the use of a chemical agent as defined above as a positive control in a test for evaluating the toxicity, preferably the neurotoxicity, of a compound.

The evaluation test preferably comprises the incubation of a cell system with the test compound for a period exceeding 48 h, preferably at least 60 h.

An additional object of the present invention is a method for evaluating the toxicity, preferably the neurotoxicity, of a compound, said method comprising the steps of:

a) conducting the following incubations in parallel, for an incubation period exceeding 48 h, preferably at least 60 h:
  i) incubating a cell system with an incubation solution comprising the test compound,
  ii) incubating a cell system with an incubation solution comprising a control compound, said control compound being the chemical agent as described above, and
  iii) incubating a cell system with an incubation solution containing no test compound or control compound, b) for each system incubated in step a), quantifying a specific marker of neurotoxicity, and c) comparing the values obtained in step b) in order to determine the toxicity of the compound.

Incubations ii) and iii) respectively correspond to positive and negative control experiments. The cell systems used in steps i), ii), and iii) are identical. For example, for the implementation of steps i), ii), and iii), zebrafish larvae may be used. The cell system used in the method according to the invention is preferably a neuronal cell culture, from a cell line of neuronal origin or nervous tissue, preferably brain tissue. Preferably, the cell system is a cell line, preferably of neuronal origin and/or presenting one or more biochemical characteristics of dopaminergic neurons. For example, the cell line is selected from the lines SH-SY5Y, SK-N-MC, and PC12.

In other embodiments, the cell system is selected from a non-human animal, preferably a nematode such as *C. elegans* or a fish such as the zebrafish, in the adult or larval state.

An incubation time exceeding 48 h encompasses an incubation period of at least 54 h, at least 60 h, at least 66 h, at least 72 h, at least 78 h, at least 84 h, at least 90 h, and at least 96 h.

As an example, step c) may be performed as follows:

First, the values obtained for incubations ii) and iii) are compared. If a variation of less than X % is obtained for these values, the test is considered to have been carried out incorrectly and must be performed, possibly with an increase in the incubation time. However, if there is a variation of more than X % between the values obtained for incubations ii) and iii), the test is considered to have been carried out correctly and the values obtained for incubations i) and iii) can be compared. If a variation of more than Y % is obtained for values i) and iii), one can conclude that the test compound is toxic.

The X and Y variation threshold values depend on the marker being quantified. In general, these values are between 5 and 50.

Without being bound by any theory, the Applicant believes that the method for evaluating the toxicity according to the invention, using furosemide pyridinium or one of its derivatives as a positive control and implementing a long incubation time, will identify neurotoxic compounds which are not identified as such by the tests currently in use. This test may have applications in identifying the neurotoxic potential of environmental pollutants—such as herbicides, pesticides, and drug residues—to which humans have general chronic exposure over a long period at low doses.

The invention also relates to a kit for evaluating the toxicity, preferably the neurotoxicity, of a compound, said test comprising:

furosemide pyridinium or one of its salts, prodrugs, metabolites, or derivatives, preferably a compound of formula (I) or (Ia), as a control compound, a cell system, optionally, one or more consumables such as culture medium, buffer solution, or a microplate, optionally, an instructional booklet describing how to conduct the test, and optionally, one or more means for the detection or quantification of a marker of toxicity.

In the uses, method, and kit for evaluating the toxicity of a compound described above, the cell system is preferably a neuronal cell culture, a cell line, preferably of neuronal origin, such as a neuroblastoma line, or nervous tissue, preferably brain tissue. Preferably, the cell system is selected from the cell lines SH-SY5Y, SK-N-MC, and PC12.

In other embodiments, the cell system is selected from a non-human animal, preferably a nematode such as *C. elegans* or a fish such as the zebrafish, in the adult or larval state.

The toxicity markers include, but are not limited to, an increase in caspase activity, an increase in cell death rate, a decrease in mitochondrial activity, an increase in the production of reactive oxygen species, an increase in the intracellular amount of α-synuclein, a decrease in mobility, and a degeneration of dopaminergic neurons.

The toxicity marker or markers to be quantified depend on the cell system chosen. For example, when using *C. elegans* or a zebrafish larva as the cell system, one analyzes the effect of the test compound on mobility, degeneration of dopaminergic neurons, and/or accumulation of alpha-synuclein. Alternatively, if using the SH-SY5Y cell line, the toxicity of the compound can be determined by quantifying caspase activity, such as caspase-3 and/or -9 activity, the intracellular amount of alpha-synuclein, the activity of complex I of the mitochondrial respiratory chain, and/or the cell survival rate at the end of incubation.

Compounds of the Invention

The invention also concerns a compound of formula (I):

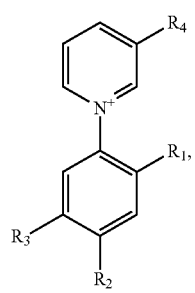

(I)

wherein:
- $R_1$ represents a hydrogen atom, a halogen atom, a $C_1$-$C_4$ alkyl, —OH, —CN, —C(=O)NH$_2$, —CF$_3$, —C(=O)O$^-$, or —C(=O)O—R$_5$ where R$_5$ represents —H or a $C_1$-$C_4$ alkyl,
- $R_2$ is —SO$_2$NH$_2$, a $C_1$-$C_4$ alkyl, a hydrogen atom, a halogen atom, —OH, —CN, —C(=O)NH$_2$, —CF$_3$, or —C(=O)OR$_6$ where R$_6$ represents H or an alkyl in $C_1$-$C_4$,
- $R_3$ is H, a halogen atom, an alkyl in $C_1$-$C_4$, —OH, —CN, —C(=O)NH$_2$, —CF$_3$, or —C(=O)OR$_7$ where R$_7$ represents H or a $C_1$-$C_4$ alkyl, and
- $R_4$ represents a hydrogen atom, —OH, or —OCH$_3$, or a pharmaceutically acceptable salt thereof.

In the meaning of the invention, a halogen atom encompasses Br, Cl, I, or F, preferably Br and Cl.

A $C_1$-$C_4$ alkyl group encompasses the methyl, ethyl, propyl, and butyl groups.

Of course, the chemical agent comprises the necessary counteranion(s) or countercation(s) depending on the ionization state of groups $R_1$, $R_2$, $R_3$ and $R_4$.

In certain embodiments of the invention, the compound of formula (I) is such that:
- $R_1$ is —H, a halogen atom, —CN, —C(=O)NH$_2$, —CF$_3$, —C(=O)O$^-$, or —C(=O)OR$_5$ where R$_5$ represents —H or a $C_1$-$C_4$ alkyl,
- $R_2$ is —SO$_2$NH$_2$, —C(=O)NH$_2$, a halogen atom, —H, —CN, or CF$_3$,
- $R_3$ is —H, a halogen atom, —CN, —CONH$_2$, —CF$_3$, —C(=O)O$^-$, or —C(=O)OR$_7$ where R$_7$ represents —H or a $C_1$-$C_4$ alkyl, and
- $R_4$ is —OH, —OMe, or —H, with the proviso that $R_2$ is not —SO$_2$NH$_2$ when $R_1$ represents —C(=O)O$^-$ or —(C=O)OH, $R_3$ is and $R_4$ is OH.

In another embodiment of the invention, the compound of formula (I) is such that:
- $R_1$ is —H, a halogen atom, —CN, —C(=O)NH$_2$, —CF$_3$, —C(=O)O$^-$, or —C(=O)OR$_5$ where R$_5$ represents —H or a $C_1$-$C_4$ alkyl,
- $R_2$ is —SO$_2$NH$_2$, —C(=O)NH$_2$, a halogen atom, —H, —CN, or CF$_3$,
- $R_3$ is —H, a halogen atom, —CN, —CONH$_2$, or —CF$_3$, and
- $R_4$ is —OH, —OMe, or —H, with the proviso that $R_2$ is not —SO$_2$NH$_2$ when $R_1$ represents —C(=O)O$^-$ or —(C=O)OH, $R_3$ is and $R_4$ is OH.

In an additional embodiment, the chemical agent is a compound of formula (I) wherein:
- $R_1$ represents a hydrogen atom, —C(=O)O$^-$, or —C(=O)O—R$_5$ where R$_5$ is H or a $C_1$-$C_4$ alkyl group,
- $R_2$ is —SO$_2$NH$_2$, a hydrogen atom, or a halogen atom,
- $R_3$ is H or a halogen atom, and
- $R_4$ is —OH or —H, with the proviso that $R_2$ is not —SO$_2$NH$_2$ when $R_1$ represents —C(=O)O$^-$ or —(C=O)OH, $R_3$ is and $R_4$ is OH, or a pharmaceutically acceptable salt thereof.

In certain embodiments, $R_4$ is —OH.

The invention also concerns a compound of formula (Ia)

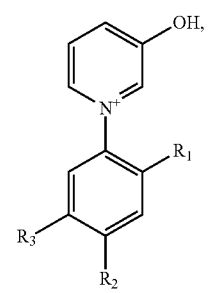

(Ia)

wherein:
- $R_1$ represents a hydrogen atom, —C(=O)O$^-$, or —C(=O)O—R$_5$ where R$_5$ is H or a $C_1$-$C_4$ alkyl group,
- $R_2$ is —SO$_2$NH$_2$, a hydrogen atom, or a halogen atom, and
- $R_3$ is H or a halogen atom, with the proviso that $R_2$ is not —SO$_2$NH$_2$ when $R_1$ represents —C(=O)O$^-$ or —(C=O)OH and $R_3$ is —Cl, or a pharmaceutically acceptable salt thereof.

The following examples are intended to more fully illustrate the invention without limiting its scope.

Examples

Part A: Chemistry

The MPP+ was purchased in the form of iodide salt from Sigma-Aldrich (CAS: 36913-39-0). The furosemide was purchased from TCI Europe N.V. (CAS number: 54-31-9).

1—Synthesis of Furosemide Pyridinium

The furosemide pyridinium was synthesized from furosemide as described in Laurence et al., Tetrahedron, 2011.

Synthesis of 4-Chloro-2-[(2,5-dimethoxy-2,5-dihydro-furan-2-ylmethyl-amino]-5-sulfamoyl-benzoic acid (compound (1))

In an undivided glass cell fitted with two carbon electrodes, furosemide (250 mg, 0.75 mmol), ammonium bromide (61 mg, 0.6 mmol), and tetraethylammonium tetrafluoroborate (81 mg, 0.4 mmol) were dissolved in methanol (10 mL). The reaction mixture was kept under magnetic stirring and a constant current of 30 mA until 2.5 F/mol was consumed. The solution was transferred into a flask and the methanol was evaporated at reduced pressure. The obtained residue was re-suspended in ethyl acetate and the inorganic salts were removed by filtration. After evaporation of the ethyl acetate, a beige solid was obtained containing a 50:50 ratio of two diastereoisomers (268 mg, 91%).

$^1$H NMR (400 MHz, acetone-d6): δ=8.55 (s, 2H), 7.07 (s, 1H), 7.05 (s, 1H), 6.22-6.15 (m, 2H), 6.05 (d, J=13.4 Hz, 1H), 6.03 (d, J=13.5 Hz, 1H), 5.79 (br s, 1H), 5.52 (br s, 1H), 3.72-3.61 (m, 2H), 3.57-3.47 (m, 2H), 3.45 (s, 3H), 3.31 (s, 3H), 3.20 (s, 3H), 3.12 (s, 3H);

$^{13}$C NMR (acetone-d6): δ=169.3, 169.1, 154.8, 154.5, 138.0, 137.8, 135.0, 135.0, 134.2, 134.2, 132.4, 132.1, 127.4, 127.2, 114.9, 114.7, 114.6, 114.0, 109.9, 108.6, 108.5, 56.4, 56.0, 50.7, 50.4, 50.1, 49.9; IR: 3257, 1674, 1595, 1503, 1455, 1331, 1229, 1162, 1043, 1012, 957, 899, 832, 799, 686, 626, 579 cm$^{-1}$;

FIRMS m/z calculated for $C_{14}H_{18}ClN_2O_7S$ [M+H]+: 393.0523. Measured: 393.0445.

Synthesis of Furosemide Pyridinium

The furosemide pyridinium was obtained by dissolving compound (1) (136 mg, 0.3 mmol) in 2 mL of TFA/MeCN mixture 60/40. The reaction mixture was maintained at a temperature of 40° C. while stirring. The precipitate was collected by filtration. A white solid of furosemide pyridinium was obtained.

Melting point: 258-260° C.;

$^1$H NMR (100 MHz, DMSO-d6): δ=8.78 (br s, 1H), 8.59 (br s, 1H), 8.50 (s, 1H), 8.09 (s, 1H), 8.00e7.87 (m, 4H);

$^{13}$C NMR (100 MHz, DMSO-d6): δ=164.8, 158.0, 143.2, 142.7, 134.9, 134.4, 133.1, 133.1, 131.5, 131.4, 129.8, 127.4; IR: 3096, 1613, 1573, 1494, 1379, 1321, 1252, 1155, 1026, 963, 927, 865, 805, 694, 654, 603, 584 cm$^{-1}$;

HRMS m/z calculated for $C_{12}H_{10}ClN_2O_5S$ [M+H]+: 328.9999. Measured: 328.9995, Anal, calculated for $C_{12}H_9ClN_2O_5S_4 2H_2O$: C, 39.51%, H, 3.59%, N, 7.68%. Measured: C, 39.47%, H, 3.61%, N, 7.46%.

2. Synthesis of Analogs of Furosemide Pyridinium

By way of example, the synthesis of two analogs of furosemide pyridinium is presented below. Additional analogs were prepared by similar methods.

Preparation of an analog of formula I wherein $R_4$ is OH: 1-(4-chlorophenyl)-3-hydroxypyridinium chloride (i) Reductive Amination:

Into a round-bottom flask were introduced 3.00 g (14.45 mmol, 1 eq) of 4-chloro-aniline, 2.4 ml (28.9 mmol, 2 eq) of distilled furfural, and 2.73 g (43.35 mmol, 3 eq) of sodium cyanoborohydride in 50.0 mL acetonitrile. Then 396 μl (6.94 mmol, 0.48 eq) of acetic acid were added. This addition was repeated 1 hour after the start of the reaction. The mixture was heated to 40° C. and stirred overnight. After evaporation of the acetonitrile, the reaction mixture was dissolved in 30 ml of tetrahydrofuran, then 8 equivalents of $NaHSO_3$ to saturation in water (s=420 g/L) were added in order to eliminate residual furfural. The mixture was stirred vigorously at 40° C. for 4 h. At the end of the reaction, the organic phase was extracted with diethyl ether and dried by $Na_2SO_4$, then filtered over a frit. After evaporation of the solvent, the 4-chloro-N-(furan-2-ylmethyl) aniline was purified by reverse-phase flash chromatography (C18 column, eluent: methanol/water, 2/8→8/2) (2.81 g, 94%).

(ii) Protection Reaction:

Into a round-bottom flask were introduced 1.41 g 4-chloro-N-(furan-2-ylmethyl) aniline (6.8 mmol, 1 eq) and 1.75 mL di-tert-butyl dicarbonate (8.16 mmol, 1.2 eq) in 20 mL distilled tetrahydrofuran. The mixture was stirred under tetrahydrofuran reflux (~70° C.) for 2 days. At the end of the reaction, the product was recovered by extraction with dichloromethane and the residual di-tert-butyl dicarbonate was hydrolyzed by washing with a solution of 0.1M HCl. The organic phase was dried by $Na_2SO_4$ before filtering over a frit. After evaporation of the solvent, the tert-butyl (furan-2-ymethyl) (4-chloro-phenyl) carbamate was purified by reverse-phase flash chromatography (C18 column, eluent: methanol/water, 2/8→8/2) (1.96 g, 93%).

(iii) Electrochemical Oxidation and Hydrolysis:

The electrolysis was carried out at room temperature in an undivided cell where the anode and cathode were carbon graphite plates. The tert-butyl (furan-2-ymethyl) (4-chlorophenyl) carbamate (719 mg; 2.34 mmol), the supporting electrolyte: tetraethylammonium tetrafluoroborate (75 mg; 0.37 mmol), and the redox mediator: ammonium bromide (295 mg, 3.04 mmol) were introduced into the cell and dissolved in 25 mL methanol. The electrodes were then inserted into the cell and connected to a generator, and the applied current intensity was set at 20 mA. The reaction mixture was homogenized by magnetic stirring. The electrolysis was followed by GC analysis of samples of the reaction medium, and was stopped when the tert-butyl (furan-2-ymethyl) (4-chloro-phenyl) carbamate was completely consumed. At the end of the electrolysis, the cell contents were transferred into a round-bottom flask. After evaporating the solvent, the crude reaction product was taken up in diethyl ether; the supporting electrolyte precipitated. After filtration, the ether phase was evaporated and the oil obtained was treated in acid medium by a THF/HCl mixture (5N). After reaction, the 1-(4-chlorophenyl)-3-hydroxypyridinium chloride was obtained by evaporation of the reaction mixture, precipitation in ethyl acetate, and filtration (226 mg, 40%).

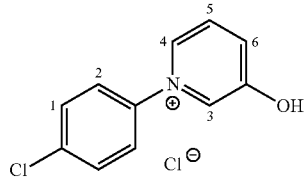

Appearance: white powder, Melting Point: 176.2° C.

IR: 3375 (O—H), 3132 (=CH), 3088 (=CH), 3052 (=CH), 1560 (C=C), 1470 (C=C), 1386 (O—H), 1288 (O—H), 1258 (C—O), 1212 (C—O), 894 (C—H), 833 (C—H), 795 (C—H) cm$^{-1}$.

$^1$H NMR (400 MHz, DMSO-d6): δ=8.80 (s, 1H, H-3), 8.76 (d, $J_{4-5}$=8 Hz, 1H, H-4), 8.17 (d, $J_{6-5}$=9 Hz, 1H, H-6), 8.08 (dd, $J_{5-4}$=8 Hz, $J_{5-6}$=9 Hz, 1H, H-5), 7.89 (d, $J_{1-2}$=8 Hz, 2H, H-1), 7.83 (d, $J_{2-1}$=8 Hz, 2H, H-2).

$^{13}$C NMR (100 MHz, DMSO-d6): δ=157.1, 141.5, 135.9, 135.8, 133.2, 132.4, 130.0, 128.5, 126.6.

LC/MS m/z (%) (Betasil Phenyl-Hexyl column 150 mm (150 mm×2.1 mm×3 μm), elution: MeOH/aqueous formic acid buffer solution (50/50), isocratic mode, D=0.2 mL/min, Rt=2.29 min, mode ESI+, calculated for $C_{11}H_9ClNO^+$ [M]+: 206.04 (100.0%), 208.03 (32.0%), 207.04 (12.0%), 209.04 (3.9%); measured 206.15 (100.0%), 208.16 (29.9%), 207.20 (11.6%), 209.20 (3.7%).

Elemental analysis calculated for $C_{11}H_9Cl_2NO$. 5/4 $H_2O$: C, (49.93%), H, (4.38%), N, (5.29%); measured: C, (50.18%), H, (4.08%), N, (5.82%).

Preparation of an analog of formula I where $R_4$ is H: 1-(4-chlorophenyl) pyridinium chloride (i) Preparation of the Zincke Salt:

Into a Schlenk flask were introduced 2.00 g (9.90 mmol, 1 eq) of 1-chloro-2,4-dinitrobenzene and 0.80 mL (9.90 mmol, 1 eq) of pyridine in 50 mL acetone. The mixture was left to stir while heated at 60° C. for two days. Initially the solution was red, then changed to an orange tint; the 1-(2,4-dinitrophenyl) pyridinium chloride precipitated, was recovered by filtration on a frit, and was washed with diethyl ether (2.42 g, 87%).

(ii) Transamination Reaction:

Into a Schlenk flask were introduced 400 mg (1.42 mmol, 1 eq) of 1-(2,4-dinitrophenyl) pyridinium chloride and 1.1 g (8.54 mmol, 6 eq) of 4-chloroaniline in 15 mL ethanol. The mixture was left to stir while heated at 85° C. for ten days. After evaporation of the solvent, the 1-(4-chlorophenyl) pyridinium chlorine precipitated in ethyl acetate and was collected by filtration on a frit (225 mg, 70%).

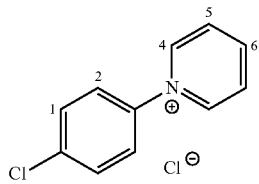

Appearance: light brown powder, Melting Point: 123.4° C.

IR: 3363 (O—H), 3115 (=CH), 3093 (=CH), 3020 (=CH), 1590 (C=C), 1474 (C=C), 1409 (O—H), 1361 (O—H), 1304 (O—H), 1261 (C—O), 1218 (C—O), 870 (C—H), 843 (C—H), 777 (C—H) cm$^{-1}$.

$^1$H NMR (400 MHz, DMSO-d6): δ=9.34 (d, $J_{3-4}$=8 Hz, 2H, H-3), 8.80 (t, $J_{5-4}$=8 Hz, 1H, H-5), 8.32 (t, $J_{4-3}$=$J_{4-5}$=8 Hz, 2H, H-4), 7.94 (d, $J_{1-2}$=8 Hz, 2H, H-1), 7.86 (d, $J_{2-1}$=8 Hz, 2H, H-2) ppm.

$^{13}$C NMR (100 MHz, DMSO-d6): δ=146.8, 145.0, 141.5, 136.0, 130.0, 128.0, 126.8.

LC/MS m/z (%) (Betasil Phenyl-Hexyl column 150 mm (150 mm×2.1 mm×3 μm), elution: MeOH/aqueous formic acid buffer solution (50/50), isocratic mode, D=0.2 mL/min, Rt=2.29 min, mode ESI+, calculated for $C_{11}H_9ClN^+$ [M]$^+$: 190.04 (100.0%), 192.04 (32.0%), 191.05 (12.0%), 193.04 (3.9%); measured 190.18 (100.0%), 192.21 (30.8%), 191.23 (12.3%), 193.20 (3.2%).

Elemental analysis calculated for $C_{11}H_9Cl_2N$. $H_2O$: C, (54.12%), H, (4.54%), N (5.74%); measured: C, (54.55%), H, (4.58%), N, (5.72%).

Part B: Biological Evaluations

Materials and Methods

1. Cell Culture

Cells from SH-SY5Y human neuroblastomas were cultured in a DMEM medium containing 4.5 g·L$^{-1}$ glucose, 10% fetal calf serum, and 1% penicillin/streptomycin, and placed in an incubator at 37° C. with 7% $CO_2$.

In the various experiments, the SH-SY5Y cells were seeded at a density of 4×10$^4$ cells/mL. 24 h after seeding, the cells were exposed to the various test compounds at 37° C. for 24 h, 48 h, 72 h, or 96 h.

Skin fibroblasts were obtained from a skin biopsy from the back of young Wistar rats (3 months old). Biopsies were cut tangentially to the epidermis in order to separate the superficial and deep dermal fibroblasts. The cells were grown in DMEM containing 4500 mg/L glucose, 20% FCS, and 100 IU/ml penicillin/streptomycin, at 37° C. with 5% $CO_2$. The cells were used at the third passage (Yue et al., CDD, 2009).

2. Cell Viability Test in MTT

This test consisted of rapidly measuring cellular metabolic activity in the presence of the study compound at different concentrations, in order to conduct a dose-response study. To do this, the tetrazolium salt MTT, 3-(4,5-dimethylthiazol-2-yl)-2,5-diphenyltetrazolium bromide (Amoroso et al., Biochim Biophys Acta, 1999, 1452(2):151-60), was placed in contact with the cells. MTT is reduced to formazan by living cells that have the capacity to metabolize it, unlike dead cells. To conduct this test, SH-SY5Y neuronal cells in 48-well plates were incubated for 24 h, 48 h, 72 h, and 96 h, with furosemide pyridinium at concentrations ranging from 0 to 1000 μM. Then MTT (0.5 mg/ml final) was added to each well and incubated at 37° C. for 2 h. At the end of incubation, after carefully removing the medium, DMSO was added (200 μL) to dissolve the cell membranes and the formazan crystals formed by the living cells. The toxicity of the molecule was evaluated by determining the amount of reduced MTT, doing so by measuring the absorbance at 550 nm as this value is proportional to the number of living cells. The results were expressed as a function of the values obtained for cells treated only with the solvent used to dissolve the compound of interest. To compare the toxicity of furosemide pyridinium to that of MPP+, the cells were incubated in the presence of MPP+ (0 to 1000 μM) for 6 h. The culture medium was replaced and the cells were incubated at 37° C. for an additional 24 h (no MPP+). Cell survival was measured at the end of these 24 hours of incubation as described above. When evaluating the effect of different concentrations of α-tocopherol (vitamin E), a membrane antioxidant, the cells were pretreated for 24 h with this antioxidant before being exposed to furosemide pyridinium at a concentration of 0.5 mM under the same experimental conditions as above.

3. Activity of Caspase-9, -3, and -8 (Yue et al., Cell Death Differ, 2009, 16(5):770-81)

Measurement of the activities of the various caspases is based on the ability of the caspases to cleave specific fluorescent substrates: Ac-DEVD-AFC for caspase-3, Ac-IETD-AFC for caspase-8, or Ac-LEHD-AFC for caspase-9. SH-SY5Y neuronal cells were incubated in 48-well plates with either furosemide pyridinium (1 mM) for 96 h or with MPP+ (1 mM) for 6 h, then 24 h of incubation with no MPP+. After incubation, the cells were trypsinized, then rinsed with PBS and counted, then harvested in 100 μl of buffer containing 30 mM HEPES, 0.3 mM EDTA, 100 mM NaCl, 0.15% Triton X-100, and 10 mM DTT. The cell extract was then incubated for 1 hour at 37° C. with the specific substrate (100 μM) in a 96-well plate. Fluorescence was measured at $\lambda_{ex}$400 nm and $\lambda_{em}$505 nm in a fluorescence detection plate reader (TECAN Infinite M1000) (Yue et al., supra). The results were expressed as percentages relative to the measured activity of cells cultured under the same conditions and not subjected to any treatment.

4. Cellular Accumulation of α-Synuclein (Lehri-Boufala et al., Submitted)

Cells were incubated under the same conditions as above with furosemide pyridinium (1 mM, incubation: 96 h) and MPP+ (1 mM, incubation: 6 h, wait 24 h). After incubation, the cells were trypsinized, rinsed with PBS, counted, then harvested in 100 μl of buffer containing: 250 mM sucrose; 70 mM KCl; 137 mm NaCl; 4.3 mm $NaH_2PO_4$; 1.4 mm $KH_2PO_4$, pH 7.2; and 250 m/ml digitonin. Incubation at 4° C. was then conducted for 5 minutes before centrifuging at 13,000 g for 5 minutes to separate the cytosolic and lysosomal fraction from the mitochondrial fraction. Deposits of cytosolic fraction in the Western blot were adjusted according to the number of cells. The protein samples were diluted in 4× Laemmli and were then heated for 3 minutes at 95° C. to denature. They were loaded into the wells of gel. In addition to the samples, a molecular weight marker (Fermentas) was deposited in the gel. Migration was carried out in running buffer (25 mM Tris, pH 8, 192 mM glycine, 2% SDS—20%) at room temperature at 100V until the blue migration front reached the bottom of the gel. The transfer was carried out on PVDF membrane. The transfer was done in transfer buffer (25 mM Tris, 192 mM glycine, 10% methanol) overnight at 4° C. and 30V or for 2 hours at 4° C. and 80V. Saturation of the membrane was achieved with 1×PBS/0.2% Tween/3% milk for 1 hour at room temperature. Then the membranes were immunolabeled for 1.5 h at room temperature with a primary antibody diluted in 1×PBS/0.2% Tween/3% milk. After 3 washes in 1×PBS/0.2% Tween, the immunolabeling was revealed after incubation for 1 h at room temperature with a secondary antibody conjugated to HRP (horseradish peroxidase). The use of a P chemiluminescent substrate that reacts with peroxidase revealed the presence of the protein of interest on the membrane after placement of photo film for a specific period of time. The primary antibody used was anti-α-synuclein, 1:500 (visualized with an anti-rabbit secondary antibody, 1:10,000).

5. Extraction of Rat Brain Mitochondria (Brain Res, May 4, 2001, 900(1):72-9)

To extract the mitochondria, a rat was anesthetized with 2% Rompun (100 µl/100 g) using an anesthetic dose that does not modify activity of the mitochondrial respiratory chain. The animal was then decapitated in order to collect from the brain either the cortex or the striatum, which were quickly placed in a Potter Elvejhem® containing 6 ml of extraction buffer at 4° C. (250 mM sucrose, 40 mM KCl, 2 mM EGTA, 1mg/ml BSA, 20 mM Tris, pH=7.2). This mixture was homogenized to break open the cells and release the mitochondria and then centrifuged at 2000 g for 8 minutes to remove the larger membrane debris and the nuclei from the pellet. The supernatant was then recovered and centrifuged at 13,000 g for 11 minutes. The supernatant was discarded while the pellet containing a mitochondria-rich fraction was resuspended in 500 µl of respiration buffer at 4° C. (300 mM D-mannitol, 10 mM KCl, 10 mM $KH_2PO_4$, 5 mM $MgCl_2$, pH=7.2). The total protein concentration was assayed by the Bio-Rad® BCA technique in order to adjust/normalize the amount of mitochondrial proteins used in the experiments.

6. Measurement of Oxygen Consumption and Respiratory Chain Function (Morin et al., Neurosciences, 2002, 115(2):415-24)

Added to the polarography chamber (Hansatech) were 30 µl of mitochondria solution (0.2 mg), 460 µL of respiration buffer, 5 µl of test compound solution (meaning MPP+ or furosemide pyridinium) (or its solubilizing solvent). Then 5 µl of a 10/10 mM mixture of malate-pyruvate substrates were added, which allowed the respiratory chain to function (stage 2) starting from complex I. After about 40 seconds, 5 µl of 200 µM ADP were added, resulting in an increase in oxygen consumption as the ADP activated complex V (stage 3). Once all the ADP was consumed, the oxygen consumption returned to an initial stage (stage 4) that is equivalent to stage 2. The effect of the compound on respiratory control was evaluated (ratio of stage 3 to 4), which corresponds to the coupling of the respiratory chain, or in other words the ATP synthesis at complex V and the oxygen consumption due to complexes I to IV. The results are expressed as percentages of the value measured for mitochondria not treated with the test compound (but treated with the solubilizing solvent).

After examining the general respiratory chain function, complex I was blocked by adding rotenone in order to determine the complex targeted by the molecule. The same protocol was used but with the addition of 10 mM succinate, then 2 µM rotenone. Succinate has the effect of induction of complex II of the respiratory chain, by facilitating the passing of FADH at this complex, while rotenone inhibits complex I.

7. Spectrophotometric Analysis of Complex I Activity

The kinetics of the oxidation reaction of NADH into NAD+ at 340 nm at 37° C. were continuously monitored by spectrophotometry using a JASCO V-530 spectrophotometer or a TECAN 1000M Infinite plate reader, set to a wavelength of 340 nm for 3 min. The amount of mitochondria extract to obtain the maximum activity introduced into the reaction volume was 100 µg with the spectrophotometer and 10 µg with the reader. Each manipulation must be done at substrate saturation, which is an NADH concentration of 160 µM. Mitochondria previously divided into multiple aliquots were frozen, then quickly thawed a few minutes before use. In a first step, the mitochondria extract was introduced into the hypotonic buffer (50 mM $KH_2PO_4$ and 10 mM MgCl2, pH=7.2 at 37° C.) for 2 minutes to break open the mitochondrial membranes and access the respiratory chain (Chretien et al., Biochem Biophys Res Commun, 2003, 301(1):222-4). Bovine serum albumin (3.5 mg/ml), decylubiquinone (10 Mm), KCN, (10 mM), and NADH were added before beginning to record the kinetics. Bovine serum albumin optimizes complex I activity (Chretien et al., supra; Janssen et al., Clin Chem, 2007, 53(4):729-34). The decylubiquinone replaces the natural acceptor of complex I electrons: coenzyme Q10 or ubiquinone. Cyanide is an inhibitor of complex IV of the respiratory chain. The slope of the kinetics was then measured. The results obtained in the presence of the compound of interest were compared to the controls conducted with only the solvent of the compound. The inhibition percentage was then calculated.

Results

1. Evaluation of Cell Viability, MTT Assay

After 24 h of incubation, furosemide pyridinium had no significant effect on cell survival, even at a 1 mM concentration. Conversely, MPP+ induced massive cell death at a 1 mM concentration after the cells were incubated for 6 h (+24 h without MPP+) (FIG. 1A). The EC50 of MPP+ was 386.2±19.2 µM.

In contrast, after 96 h of incubation with furosemide pyridinium, cell viability was reduced by approximately 60%. The EC50 of furosemide pyridinium was estimated at 0.973 µM (see FIG. 1B). Furosemide pyridinium therefore exerts a toxic effect on SH-SY5Y neuronal cells which can be observed after long exposure.

FIGS. 1A and 1B clearly illustrate the difference in cell toxicity between MPP+ and furosemide pyridinium.

2. Caspase Activation

Measurements of caspase activity are shown in FIG. 1C.

The enzymatic activity of caspase-9 was significantly increased (170%) in cells treated with furosemide pyridinium for 96 h in comparison to the activity of this protease measured in untreated cells. This increase, however, is significantly lower than that observed after incubation for 24 h with MPP+. After incubation with furosemide pyridinium, the activity of caspase-3 in cells was increased significantly (179%) compared to the activity measured in untreated cells. This increase is the same as that observed after incubation with MPP+ for only 24 h with MPP+. Cells after incubation with furosemide pyridinium presented cytosolic activity of caspase-3 and -9 that was significantly higher than in untreated cells. This indicates that it is the intrinsic mitochondrial pathway of apoptosis which is activated, reducing cell survival by inducing cell death as is observed for MPP+. However, the kinetics to obtain this effect were much slower (96 h) for furosemide pyridinium than for MPP+, requiring only 6 h (+24 h without incubation with MPP+). Exposure of cells to furosemide pyridinium (96 h) or MPP+ (6 h) did not induce significant changes in caspase-8 activity. These compounds did not induce the extrinsic apoptotic pathway.

3. Cellular Accumulation of α-Synuclein

Evaluation of α-synuclein accumulation was carried out in SH-SY5Y cells, after 96 h incubation in the presence of furosemide pyridinium or DMSO (solubilizing solvent —control). In parallel, the accumulation of α-synuclein was determined for SH-SY5Y cells after 6 h incubation with MPP+ (+24 h without MPP+) or DMSO (control). After treating the cells, the total amount of α-synuclein was determined by immunoblotting (Western blot) to allow separating and identifying the protein of interest, α-synuclein, by a specific antibody. FIG. 2A shows the gels obtained after development, and FIG. 2B shows the result of quantification of the total accumulation of α-synuclein (in monomer, dimer, and oligomer form). A significant increase of 40% in the total amount of α-synuclein was observed in cells treated with furosemide pyridinium compared to the control cells. This increase was quantitatively much less than that induced by MPP+ (319%), despite a much longer incubation time. This confirms that furosemide pyridinium has slow toxicity kinetics in vitro, with an α-synuclein accumulation involving gradual and slow processes, probably very different from the abrupt processes induced by MPP+.

4. Effects on the Respiratory Chain Function of Rat Cerebral Cortex Mitochondria The dose-response curves for respiratory control are shown in FIG. 3A (MPP+: white circles; furosemide pyridinium: black squares). By increasing the concentration of MPP+ or furosemide pyridinium, the respiratory control of cerebral cortex mitochondria induced by malate/pyruvate was diminished. Oxygen consumption decreased in the presence of these two molecules, suggesting that they have a target in the respiratory chain.

5. Effects on the Respiratory Chain Function of Rat Striatum Mitochondria

The dose-response curves for respiratory control are shown in FIG. 3B (MPP+: white circles; furosemide pyridinium: black squares).

In the striatum, we also observed a decrease in oxygen consumption. The effect of furosemide pyridinium was greater on striatal mitochondria than on those extracted from the cortex. This suggests that furosemide pyridinium has a specificity for the striatum.

6. Effects on the Function of Respiratory Chain Complexes II-V of Rat Cerebral Cortex Mitochondria After induction of the respiratory chain function by complex II (following inhibition of complex I by rotenone), the respiratory control of cortex mitochondria was not modified even in the presence of a high concentration (1 mM) of MPP+ or furosemide pyridinium (FIG. 4A). The respiratory chain functioned normally. These experiments therefore showed that furosemide pyridinium, similarly to MPP+, alters mitochondrial function by inhibition of complex I.

7. Protective Effect of Different Compounds Against the Toxicity Induced by Furosemide Pyridinium Pretreatment of SH-SY5Y cells with α-tocopherol at concentrations of 0.01 and 0.1 μg/mL (without subsequent incubation with furosemide pyridinium) did not change cell survival. A slight increase of 20% was observed, however, for 1 μg/mL.

Incubation with 0.5 mM furosemide pyridinium induced a decrease of about 20% in cell survival. 24 h pretreatment with α-tocopherol before incubation with furosemide pyridinium increased the cell survival rate in a dose-dependent manner, with the visible effect starting at 0.1 mg/mL α-tocopherol.

This suggests that the toxicity of furosemide pyridinium on cell survival can be countered, and that it involves the production of oxygen radicals since treatment with an antioxidant such as α-tocopherol (antioxidant) is able to protect the cells.

8. Evaluation of the Effect of Furosemide Pyridinium Analogs on Complex I Activity in Vitro The ability of various furosemide pyridinium analogs to inhibit mitochondrial complex I was assessed as described in paragraph 7 of the "Materials and Methods" section above. These activity assays showed that 1-(4-chlorophenyl)-3-hydroxypyridinium induced complete inhibition of complex I activity at a concentration of 0.2 mM. It was also shown that analogs where $R_4$=H were also capable of at least partially inhibiting complex I. The inhibitory capacity of these analogs varied with the nature of substituents $R_1$, $R_2$, and $R_3$, suggesting the existence of a specific structure-activity relationship. Thus, the non-hydroxy compound 1-(4-chlorophenyl) pyridinium almost completely inhibited (95% inhibition) complex I activity. Substitution of a methyl for the chlorine in $R_2$ decreased the inhibiting effect but complex I was still 52% inhibited.

Part C: Analysis of the Chemical Model and Screening Test

1. In Vivo Evaluation of Furosemide Pyridinium in Rats

Materials and Methods

Male albino Sprague Dawley rats (adults weighing 900-1000 g) were housed in a temperature-controlled room with free access to food and water.

A platform for electrophysiological and behavioral monitoring of the rats was used. For this, a subcutaneous implant (Data Science) was placed in the rats which allowed the EEG to be recorded by telemetry, leaving the animal completely free to move about. The cage was equipped with a video camera (10 frames per second) and an infrared light to allow recordation of the animal's activity. The EEG and video sequences were recorded in sequences of 10 seconds, and a set of variables was calculated for each sequence. The use of dedicated software allowed integration of these variables over the entire recording to detect changes in the animal's activity, EEG, and circadian rhythms. Each animal served as its own control because it was recorded for 5 days prior to furosemide pyridinium administration. The solution of furosemide pyridinium (20 mg) was dissolved in dimethylsulfoxide (DMSO, 200 μl) and then diluted with water (50 ml). The solution was replaced every day and administered for 7 days in the drinking water at a dose of 20 mg/kg. The rats were then sacrificed 5 weeks after the last dose. The rats were anesthetized with pentobarbital and infused intracardially with saline (9% NaCl), then fixed with 4% paraformaldehyde. After the infusion, the brain was removed and placed in NaCl (0.9%) at 4° C. The brain was frozen in Tissue Tek immersed in a cold isopentane bath. Coronal sections of eight microns were obtained using a cryostat and were processed for immunocytochemistry (labeling the alpha-synuclein).

Results

As shown by FIGS. 5A and 5B which present the results of immunolabeling coronal sections, oral exposure to furosemide pyridinium induced a significant increase in alpha-synuclein in the striata of the animals. In addition, initial results of the behavioral study showed a significant decrease in the amplitude of the electroencephalogram five weeks after the end of treatment, in comparison to the amplitude before exposure to furosemide pyridinium (FIG. 6A). The results obtained on sleep and arousal phases do not indicate changes in these parameters due to exposure to furosemide pyridinium. Only the number of REM sleep phases significantly increased (×2) five weeks after the end of the exposure to pyridinium (FIG. 6D). This increase in the REM sleep phases is frequently observed in patients suffering from Parkinson's disease and synucleinopathies. In animal models, the obtaining of such phenomena has not yet been observed in mice after treatment with MPTP (Laloux et al., Exp Brain Res, 2008, 186(4):635-42).

2. In Vivo Evaluation of Furosemide Pyridinium in Mice

Materials and Methods

Swiss mice were divided into two groups of five animals (experimental and control). The experiments were performed independently two times. The mice of the experimental group were exposed to furosemide pyridinium for 7 days at a daily dose of 20 mg/kg. The furosemide pyridinium was administered orally in the drinking water. The mice were sacrificed 30 days after the end of the furosemide pyridinium treatment.

Immunohistochemistry:

For this, the mice were anesthetized with pentobarbital (50 mg/Kg), then an intracardiac infusion of NaCl (0.9%) was administered, followed by fixation by an infusion of 4% paraformaldehyde in 0.1M phosphate buffer, pH 7.2. The brain was removed, placed in NaCl (0.9%) at 4° C., and frozen in Tissue Tek immersed in a cold isopentane bath. Coronal sections of eight microns were obtained using a cryostat and were processed for immunohistochemistry (labeling the tyrosine hydroxylase and the Ser129-phosphorylated alpha-synuclein).

Mitochondrial Activity:

For each mouse sacrificed, cortex and striatum samples had been previously collected and processed to extract the mitochondria. The activity of the mitochondrial respiratory chain and of complex I were determined as described in Part B above, in the "Materials and Methods" subsection (without addition of furosemide pyridinium or an analog to the medium).

Results

1. For the mitochondrial activity, a decrease of 28% was observed in the respiratory control and a decrease of 49% in the activity of complex I in the respiratory chain of mitochondria from the striata of mice exposed to furosemide pyridinium, compared to the activity measured in the striata of the control animals (FIG. 7).

Exposure to furosemide pyridinium is therefore able to induce mitochondrial dysfunction in the striatum, by targeting complex I of the respiratory chain. This inhibition of the respiratory chain is still effective 30 days after the furosemide pyridinium exposure has ended.

2. For the immunohistochemistry analyses, there was a net reduction in the labeling of tyrosine hydroxylase in the striata of mice exposed to furosemide pyridinium (FIG. 8). A sharp increase of the α-synuclein phosphorylated at serine 129 was also found in the striata of mice exposed to furosemide pyridinium, by immunolabeling with an antibody specific for α-synuclein phosphorylated at this position (FIG. 9). This increase in phosphorylated α-synuclein is specific to the striatum, as no increase was observed in the cortexes of mice exposed to furosemide pyridinium.

Previous studies have shown that α-synuclein phosphorylated at Ser129 represents ~90% of the alpha-synuclein contained in Lewy bodies, while it only represents 4% of the alpha-synuclein present in healthy brain tissue (Fujiwara, H. et al., Nat Cell Biol. 2002, 4, 160-164; Anderson, J. P. et al., J Biol Chem, 2006, 281, 29739-29752). It is notable that the increase in α-synuclein phosphorylated at Ser129 has never been observed to date in the chemical models of Parkinson's disease described in the prior art (model induced by MPTP or by rotenone for example).

3. Example of Making Use of a Screening Test According to the Invention

Zebrafish embryos were raised in E3 medium (5 mM NaCl, 0.17 mM KCl, 0.33 mM $CaCl_2$, 0.33 mM MgSO4, pH 7.4) at 28.5° C. with a 14:10 h day-night cycle. The medium was replaced daily until the third dpf (day post-fertilization). After 6 dpf, the larvae were fed twice a day. For the movement analysis, the larvae were carefully transferred into the wells of a 48-well plate filled with E3 medium, using a large-bore (at least 4 mm) Pasteur pipette to avoid physical damage to the larvae. The larvae were left for 30 minutes at 28.5° C. in the plate prior to recording, to allow them to acclimate to the environment. Treatment with furosemide pyridinium was performed by exposure to different concentrations of pyridinium diluted in E3 medium, starting 48 hours after dpf of the zebrafish larvae. The test concentrations ranged from concentrations close to those found in the environment for furosemide (0.200 ng/L) to more pharmacological concentrations (1 mg/L).

In order to assess the protective potential of new drug compounds, pretreatment by an antioxidant, for example alpha-tocopherol, is conducted for the 24 hours preceding exposure to furosemide pyridinium. The screening test will then consist of combining various methodologies and approaches in order to progressively select compounds protecting against the effects of furosemide pyridinium, and to understand the biological mechanisms underlying these protective effects.

Behavioral Assessment: The first stage of the screening is conducted by measuring the behavioral effects of the molecules of interest on zebrafish larvae. Swimming ability and the movements of zebrafish larvae exposed to furosemide pyridinium are evaluated in the presence and absence of the molecules of interest. The swimming ability and movements of the larvae are evaluated using a ZebraBox® type of device. The same larvae are evaluated for the entire duration of the study, thus reducing the number of animals used in accordance with the "3R" principles of animal experiments.

Immunohistological evaluation: This screening may also be conducted by examining the presence of alpha-synuclein aggregates and Lewy bodies, as well as the degeneration of dopaminergic neurons, looking at their number and the expression of tyrosine hydroxylase. These studies are carried out by fixation and permeabilization of the larvae after treatment on the desired day, and revealing the presence of the protein of interest using specific antibodies by immunohistochemistry. The result can then be observed under a microscope or quantified in a fluorescence plate reader, and requires only a day to complete.

Biochemical evaluation: These studies are carried out on homogenates or protein extracts of zebrafish larvae. An assessment of the mitochondrial respiratory chain function, complex I activity, oxidative stress, and apoptosis can be conducted. This allows characterization of the molecular mechanism(s) of action of the evaluated compound which may potentially protect the brain tissue from forming the key biomarkers of Parkinson's disease and other synucleinopathies.

All experiments were performed in triplicate, with five to ten independent laboratory results analyzed for batteries of zebrafish from different clutches.

The invention claimed is:

1. A method for preparing a chemical model of a synucleinopathy, comprising a step of placing a cell system in contact with a compound selected from the group consisting of:
   (i) furosemide pyridinium; and
   (ii) a compound of formula (I)

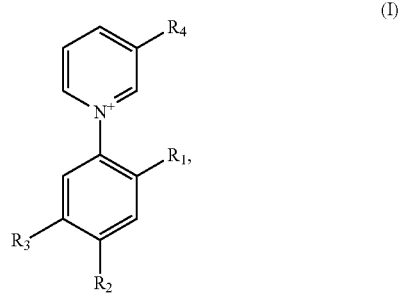

wherein:
   $R_1$ represents a hydrogen atom, a $C_1$-$C_4$ alkyl, a halogen atom, —OH, —CN, —$CF_3$, —C(=O)$NH_2$, —C(=O)O$^-$, or —C(=O)O—$R_5$ where $R_5$ represents H or a $C_1$-$C_4$ alkyl,
   $R_2$ is a hydrogen atom, a halogen atom, a $C_1$-$C_4$ alkyl, —OH, —CN, —C(=O)$NH_2$, —$CF_3$, or —C(=O)O$R_6$, where $R_6$ represents H or a $C_1$-$C_4$ alkyl,
   $R_3$ is H, a halogen atom, a $C_1$-$C_4$ alkyl, —OH, —CN, —C(=O)$NH_2$, —$CF_3$, or —C(=O)O$R_7$ where $R_7$ represents H or a $C_1$-$C_4$ alkyl, and
   $R_4$ represents a hydrogen atom, —OH, or —$OCH_3$,
or a pharmaceutically acceptable salt thereof, wherein the cell system is derived from nervous tissue or is of neuronal origin,
   and whereby the chemical model of a synucleinopathy is obtained.

2. The method of claim 1, wherein the synucleinopathy is Parkinson's disease.

3. The method of claim 1, wherein the cell system is selected from the group consisting of nervous tissue, an organotypic culture obtained from brain tissue, a culture of nerve cells, a primary neuron culture, and a cell line of neuronal origin.

4. The method of claim 1, wherein the cell system is a cell line selected from the group consisting of the cell lines SH-SY5Y, SK-N-MC, and PC12.

5. The method of claim 1, wherein the compound is furosemide pyridinium.

6. A chemical model of a synucleinopathy obtained according to the method of claim 1.

7. A method for evaluating, screening, or selecting a compound for the treatment or prevention of a synucleinopathy, said method comprising:
   a) placing a cell system in contact with a compound selected from the group consisting of:
   (i) furosemide pyridinium; and
   (ii) a compound of formula (I)

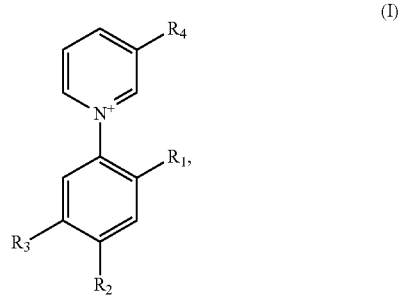

wherein:
   $R_1$ represents a hydrogen atom, a $C_1$-$C_4$ alkyl, a halogen atom, —OH, —CN, —$CF_3$, —C(=O)$NH_2$, —C(=O)O$^-$, or —C(=O)O—$R_5$ where $R_5$ represents H or a $C_1$-$C_1$ alkyl,
   $R_2$ is a hydrogen atom, a halogen atom, a $C_1$-$C_4$ alkyl, —OH, —CN, —C(=O)$NH_2$, —$CF_3$, or —C(=O)O$R_6$, where $R_6$ represents H or a $C_1$-$C_4$ alkyl,
   $R_3$ is H, a halogen atom, a $C_1$-$C_4$ alkyl, —OH, —CN, —C(=O)$NH_2$, —$CF_3$, or —C(=O)O$R_7$ where $R_7$ represents H or a $C_1$-$C_4$ alkyl, and
   $R_4$ represents a hydrogen atom, —OH, or —$OCH_3$,
or a pharmaceutically acceptable salt thereof, wherein the cell system is derived from nervous tissue or is of neuronal origin,
   b) placing said cell system in contact with the test compound, and
   c) detecting or quantifying a marker characteristic of the synucleinopathy to determine the effectiveness of the test compound for reducing the marker characteristic of the synucleinopathy,
wherein step b) may be implemented simultaneously, before, or after step a), or may overlap step a).

8. The method of claim 7, wherein the compound is furosemide pyridinium.

9. The method of claim 7, wherein:
   said cell system is selected from the group consisting of nervous tissue, an organotypic culture obtained from brain tissue, a culture of nerve cells, and a cell line of neuronal origin, and
   said marker is selected from the group consisting of an intracellular accumulation of a synuclein, a marker of apoptotic cell death, a decrease in the cell survival rate, a decrease in the activity of the mitochondrial respiratory chain, and combinations thereof.

10. A kit for implementing a method for evaluating, screening, or selecting a compound intended for the treatment or prevention of a synucleinopathy, or for the preparation of a chemical model of a synucleinopathy, comprising:
   a compound selected from the group consisting of:
   (i) furosemide pyridinium; and
   (ii) a compound of formula (I)

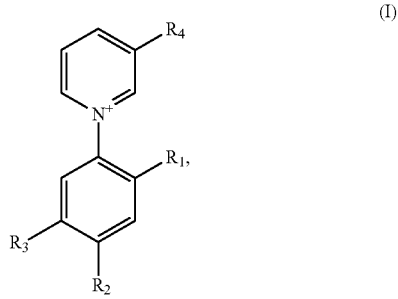

wherein:
   $R_1$ represents a hydrogen atom, a $C_1$-$C_4$ alkyl, a halogen atom, —OH, —CN, —$CF_3$, —C(=O)$NH_2$, —C(=O)O$^-$, or C(=O)O—$R_5$ where $R_5$ represents H or a $C_1$-$C_4$ alkyl,
   $R_2$ is a hydrogen atom, a halogen atom, a $C_1$-$C_4$ alkyl, —OH, —CN, —C(=O)$NH_2$, —$CF_3$, or —C(=O)O$R_6$ where $R_6$ represents H or a $C_1$-$C_4$ alkyl,
   $R_3$ is H, a halogen atom, a $C_1$-$C_4$ alkyl, —OH, —CN, —C(=O)$NH_2$, —$CF_3$, or —C(=O)O$R_7$ where $R_7$ represents H or a $C_1$-$C_4$ alkyl, and
   $R_4$ represents a hydrogen atom, —OH, or —$OCH_3$, or a pharmaceutically acceptable salt thereof and
a cell system selected from nervous tissue and a cell or a
  cell culture from nervous tissue or of neuronal origin,
  to be placed in contact with the compound in order to
  obtain said chemical model.

* * * * *

UNITED STATES PATENT AND TRADEMARK OFFICE
CERTIFICATE OF CORRECTION

PATENT NO. : 9,744,250 B2  
APPLICATION NO. : 14/443499  
DATED : August 29, 2017  
INVENTOR(S) : Thierry Martens et al.

Page 1 of 1

It is certified that error appears in the above-identified patent and that said Letters Patent is hereby corrected as shown below:

In the Specification

Column 23,  
Line 60, "$R_3$ is and $R_4$ is OH." should read --$R_3$ is –Cl and $R_4$ is OH.--.

Column 24,  
Line 5, "$R_3$ is and $R_4$ is OH." should read --$R_3$ is –Cl and $R_4$ is OH.--.

Column 24,  
Line 14, "$R_3$ is and $R_4$ is OH." should read --$R_3$ is –Cl and $R_4$ is OH.--.

Column 25,  
Line 16, "FIRMS m/z" should read --HRMS m/z--.

In the Claims

Column 36,  
Line 58, "or C(=O)O–$R_5$" should read --or –C(=O)O–$R_5$--.

Signed and Sealed this  
Third Day of July, 2018

Andrei Iancu  
*Director of the United States Patent and Trademark Office*